(12) United States Patent
Lemichez et al.

(10) Patent No.: US 7,655,240 B2
(45) Date of Patent: Feb. 2, 2010

(54) VACCINE COMPOSITION COMPRISING AN IMMUNOADJUVANT COMPOUND CONSISTING OF A RHO GTPASE FAMILY ACTIVATOR

(75) Inventors: Emmanuel Lemichez, Nice (FR); Cécil Czerkinsky, Nice (FR); Fabienne Anjuere, Nice (FR); Patrice Boquet, Villefranche-sur-Mer (FR); Patrick Munro, Nice (FR); Gilles Flatau, Nice (FR)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 240 days.

(21) Appl. No.: 10/589,505

(22) PCT Filed: Feb. 25, 2005

(86) PCT No.: PCT/EP2005/002105

§ 371 (c)(1),
(2), (4) Date: Mar. 8, 2007

(87) PCT Pub. No.: WO2005/082408

PCT Pub. Date: Sep. 9, 2005

(65) Prior Publication Data

US 2007/0172491 A1 Jul. 26, 2007

(30) Foreign Application Priority Data

Feb. 26, 2004 (EP) .................................. 04300100

(51) Int. Cl.
*A61K 39/02* (2006.01)
(52) U.S. Cl. .............. 424/190.1; 424/185.1; 424/193.1; 424/203.1; 424/253.1; 424/257.1; 530/300; 530/350
(58) Field of Classification Search ........................ None
See application file for complete search history.

(56) References Cited

U.S. PATENT DOCUMENTS 6,660,847 B1 * 12/2003 Shiozawa et al. .......... 536/23.5

FOREIGN PATENT DOCUMENTS

EP 1 342 784 A 9/2003

OTHER PUBLICATIONS

Ron et al (EMBO J. 1988. 7: 2465-2473),.*
Komai et al (Bichem. Biophys. Res. Commun.2002. 299: 455-458).*
Eva et al. (Proc, Natl. Acad. Sci USA 1988. 85: 2061-2065).*
Smith et al (Nature. 1997. 388: 539-547).*
Lan et al (Infect. Immun. 2003. 71: 6298-6306).*
Bakshi et al (J.bacteriol. 2000. 182: 2341-2344).*
Stender et al (Mol.Microbiol. 2000. 36: 1206-1221).*
McClelland et al. 2001. Nature 413: 852-856.*
Ehrbar et al (J.Baceteriol. 2003. 185: 6950-6967).*
Mirold et al (2001. J. Mol. Biol. 2001. 312: 7-16).*
Mirold et al. (Proc. Natl. Acad. Sci. USA. 1999. 96: 9845-9850).*
Parkhill et al. (Nature. 2001. 413: 848-852).*
Walker et al (Infect. Immun. 62: 3817-3828).*
Parkhill/Sharp et al (Nat.Genet. 2003. 35: 32-40).*
Pullinger et al (Infect. Immun. 1996. 64: 4163-4171).*
Lockman et al (Infect. Immun. 2022. 70: 2708-2714).*
Oswald et al (Proc. Natl. Acad. Sci. USA 1994. 91: 3814-3818).*
Felmlee et al (J. Bacteriol. 163:94-105(1985).*
Falbo et al Infect Immun. 1993. 61: 4909-4914).*
Buetow et al Nat. Struct. Biol. 2001. 8:584-588).*
Database UniProt '(Online! Nov. 1, 1996, "Cytotoxic necrotizing factor 1." Retrieved from EBI accession No. UNIPORT: Q47106.
Moreau Violaine et al: "Action can reorganize into podosomes in aortic endothelial cells, a process controlled by Cdc42 and RhoA" Molecular and Cellular Biology, vol. 23, No. 19, Oct. 2003 pp. 6809-6822.
Munro P et al: "The Rho GTPase activators CNF1 and DNT bacterial toxins have mucosal adjuvant properties" Vaccine, Butterworth Scientific. Guildford, GB, vol. 23, No. 20, Apr. 8, 2005, pp. 2551-2556.

* cited by examiner

*Primary Examiner*—Jennifer E Graser
(74) *Attorney, Agent, or Firm*—Young & Thompson

(57) ABSTRACT

This invention is based on the experimental finding that activators of Rho GTPases, namely the cytotoxic necrotizing factor 1 (CNF1), and DNT bear immunostimulatory properties towards the systemic response to orally administered ovalbumine. This invention concerns a vaccine composition including an immunoadjuvant compound, wherein the immunoadjuvant compound consists of a Rho GTPase activator.

7 Claims, 5 Drawing Sheets

VACCINE COMPOSITION COMPRISING AN IMMUNOADJUVANT COMPOUND CONSISTING OF A RHO GTPASE FAMILY ACTIVATOR

FIELD OF THE INVENTION

The present invention relates to a vaccine composition comprising an immuno adjuvant compound, wherein said immuno adjuvant compound consists of a RHO GTPase family activator.

BACKGROUND OF THE INVENTION

Vaccines have proven to be successful, highly acceptable methods for the prevention of infectious diseases. There are cost effective, and do not induce antibiotic resistance to the target pathogen or affect normal flora present in the host. In many cases, such as when inducing anti-viral immunity, vaccines can prevent a disease for which there are no viable curative or ameliorative treatments available.

Vaccines function by triggering the immune system to induce a response to an agent, or an antigen, typically in an infectious organism or a portion thereof that is introduced into the body in a non-infectious or non-pathogenic form.

Once the immune system has been "primed" or sensitised to the organism, later exposure of the immune system to this organism, results in a rapid and robust immune response that destroys the pathogen before it can multiply or infect enough cells in the host organism to cause disease symptoms.

The agent, or antigen, used to prime the immune system can be the entire organism in a less infectious state, known as an attenuated organism, or in some cases, component of the organism such as carbohydrate proteins or peptides representing various structural components of the organism.

In many cases, it is necessary to enhance the immune response to the antigens present in a vaccine in order to stimulate the immune system to a sufficient extent to make a vaccine effective, i.e., to confer immunity. Many proteins and most peptide and carbohydrate antigens, administered alone, do not elicit a sufficient antibody response to confer immunity. Such antigens need to be presented to the immune system in such a way that they will be recognized as foreign and will elicit an immune response.

To this end, additives like adjuvants, have been devised, which immobilise antigens and stimulate the immune response.

Recombinant proteins are promising vaccine or immunogenic composition candidates because they can be produced at high yield and purity and manipulated to maximize desirable activities and minimize undesirable ones.

However, because they can be poorly immunogenic, methods to enhance the immune response to recombinant proteins are important in the development of vaccines or immunogenic compositions. Such antigens, especially when recombinantly produced, may elicit a stronger response when administrated in conjunction with an adjuvant.

The best known adjuvant, Freund's complete adjuvant, consists of a mixture of mycobacteria in an oil/water emulsion.

Freund's adjuvant works in two ways; first, by enhancing cell and humoral-mediated immunity, and second by blocking rapid dispersal of the antigens challenge, also called "depot effect". However, due to frequent toxic physiological and immunological reactions to this material, Freund's adjuvant cannot be used in humans.

Another molecule that has been shown to have stimulatory or adjuvant activity is endotoxin, although known as lipopolysaccharide (LPS).

LPS stimulates the immune system by triggering an immediate immune response, a response that has evolved to enable an organism to recognize endotoxin and the invading bacteria (of which it is a component) without the need for the organism to have been previously exposed. But LPS is although too toxic to be a viable adjuvant.

Thus, there is a recognized and permanent need in the art for new compounds which can be administered with antigens in order to stimulate the immune system and generate a more robust antibody response to the antigen than will be seen if the antigens were injected alone.

Additionally, it should be noted that parenteral administration i.e. intramuscularly or sub-cutaneous, of antigens of vaccines are normally regarded as the most convenient way of administration.

However, the injection presents a range of disadvantages. It requires the use of sterile syringes and may cause pains and irritations, particularly in the case of repeated injections, including the risk of infection. More significantly, intramuscularly injections are often poorly tolerated. There is often likely to be indurations (hardening of tissue) haemorrhages and/or necrosis (local death of tissue) at the injection site. Besides, untrained person cannot administer injections.

Based on these observations, it should be noted that mucosal immunity has take a considerable importance in vaccine development because nearly all viral, bacterial and parasitic agent that cause disease of the intestinal, respiratory and genital tracks enter through the mucosal barrier. Furthermore, mucosal and systemic immune responses are often elicited and regulated independently, and induction of protective immunity at the most frequent sites of entry is likely to be most effective. Additionally, young children and elderly individuals may respond better to mucosal vaccines because the mucosal immune system develops earlier and appears to remain functional longer than the systemic compartment. Mucosal immunisations are also easier and less expensive than systemic immunisations. For example, the existence of an oral polio vaccine has allowed immunisation campaigns that may soon eradicate polio worldwide.

Accordingly, it is also an object of the present invention to provide a vaccine composition comprising an immunoadjuvant compound which could be administered by the mucosal route. These and further objects will be apparent to one ordinary skill in the art.

SUMMARY OF THE INVENTION

The present invention is based on the experimental findings that an activator of Rho GTPases, namely the cytotoxic necrotizing factor 1 (cnf1) bears immunostimulatory properties towards the systemic and mucosal responses to orally administered ovalbumine, a prototype soluble protein antigen. CNF1 consists of an injection domain (amino acid residues 1-719 of SEQ ID No 1), allowing the binding and endosomal penetration of the toxin, followed by the intracytoplasmic injection of its catalytic domain (amino acid residues 720-1014 of SEQ ID No 1), responsible for Rho GTPases protein family activation.

A first object of the invention consists in a vaccine composition comprising an immunoadjuvant compound, wherein said immunoadjuvant compound consists of a Rho GTPase activator.

In another aspect, the invention relates to a vaccine composition wherein said immunoadjuvant compound is selected from the group consisting of:
- a polypeptide comprising the amino acid sequence starting at the amino acid residue 720 and ending at the amino acid residue 1014 of sequence SEQ ID No 1,
- a polypeptide comprising the amino acid sequence starting at the amino acid residue 720 and ending at the amino acid residue 1014 of sequence SEQ ID No 2,
- a polypeptide comprising the amino acid sequence starting at the amino acid residue 720 and ending at the amino acid residue 1014 of sequence SEQ ID No 3,
- a polypeptide comprising the amino acid sequence starting at the amino acid residue 1146 and ending at the amino acid residue 1451 of sequence SEQ ID No 4,
- a polypeptide comprising the amino acid sequence SEQ ID No 5,
- a polypeptide comprising the amino acid sequence SEQ ID No 6,
- a polypeptide comprising the amino acid sequence SEQ ID No 7,
- a polypeptide comprising the amino acid sequence SEQ ID No 8, and
- a polypeptide comprising the amino acid sequence SEQ ID No 9.

The present invention also relates to a vaccine composition wherein the immunoadjuvant compound is a protein comprising a polypeptide consisting of; from the N-terminal end to the C-terminal end, respectively:
a) the injection domain of a Rho GTPase activator, and
b) the catalytic domain of a Rho GTPase activator.

1A: Immunoblots showing the kinetics of CNF1-induced activation of Rho, Rac and Cdc42 in contrast to Ras, in HUVEC. Cells were treated with $10^{-9}$M CNF1 for different periods of time. Cell lysates were subjected to GST-fusion protein pull-down assays (noted GTPases-GTP). In parallel, 2% of each cell lysate were processed for immunoblotting to monitor their cellular depletion (noted Total-GTPases).

1B: Quantification of the CNF1-induced Rho protein activation. Immunoblots were scanned and quantified using N.I.H. Image 1.6. The level of activated Rho proteins was compared to the total Rho GTPase level present in 2% of control cell lysates (mean value of three independent experiments±SD).

1C: Immunoblots showing the interference of native CNF1 and catalytic inactive CNF1-C866S on cell signaling. HUVEC were treated with "$10^{-9}$M" CNF1 or CNF1-C866S for the indicated periods of time, prior to immunoblotting analysis. MAP kinase signaling was investigated using anti-phosphop44/42 MAP Kinase (noted P-p44/42) and anti-phospho-p38 MAP Kinase (noted P-p38) antibodies. Jun kinase activity was investigated by anti-phospho-c-jun (noted P-c-jun) immunoblotting. NF-kappaB signaling pathway activation was investigated by following the IkBα cellular depletion on immunoblots.

Figure 2:
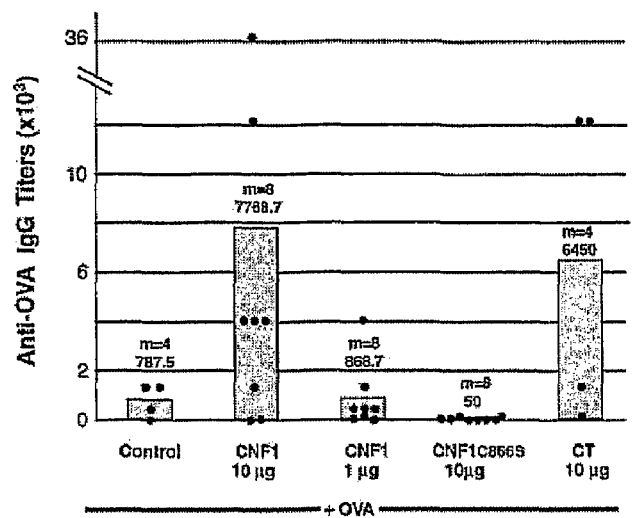

FIG. 2: Catalytic Active CNF1 Stimulates Serum IgG Responses to Orally Administered Ovalbumin (OVA).

Five groups of mice were fed OVA alone (control) or co-administered with either CNF1 (1 or 10 μg) or CNF1-C866S (10 μg) or CT (10 μg). Groups of eight mice were immunized with CNF1 or CNF1-C866S, whereas groups of four mice were immunized with OVA alone or OVA+CT. Groups of mice were challenged once, 2 weeks after the first immunization and sera collected 30 days after the first immunization. Levels of the seric anti-OVA IgG titers are expressed as geometric means (histogram and mean values) of the total IgG titers. These results are representative of two independent experiments. Anti-OVA IgG titers from individual animals are displayed (•).

Figure 3:
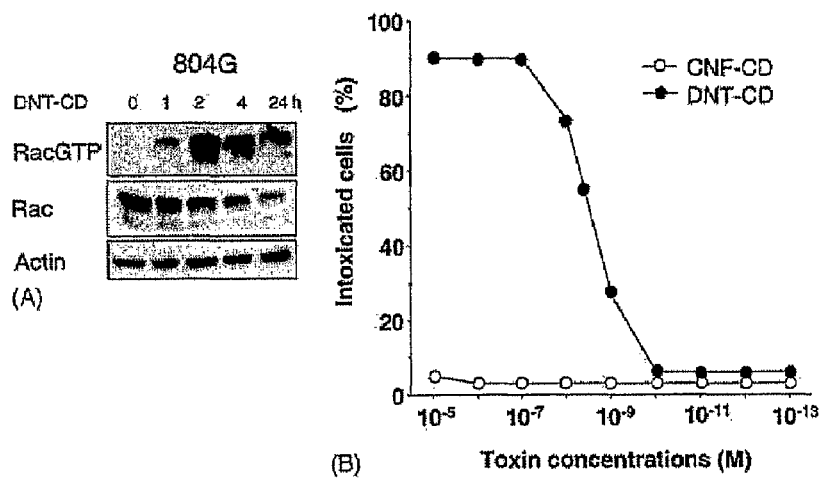
Figure 3:
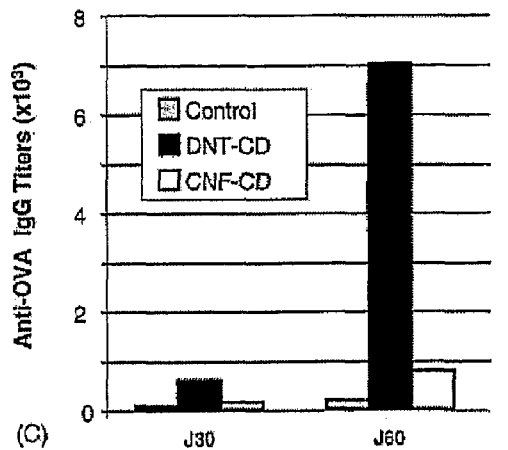

FIG. 3 DNT Catalytic Domain Stimulates Serum IgG Responses to Orally Administered Ovalbumin (OVA).

3A: Immunoblots showing the kinetics of DNT-Cd induced activation and cellular depletion of Rac. 804G cells were treated with 100 μg of DNT-CD and processed for activated Rac measurements by GST-Pak pull-down (noted RacGTP). Immunoblotting of 10 μg of total lysate was performed to visualize DNT-CD induced Rac depletion (noted Rac) and equal quantities of proteins engaged in the GST pull-down (actin).

3B: Comparison of the cellular activities of CNF-CD and DNT-CD. The graph illustrates the percentage of HEp-2 multinucleated cells measured 48 h following intoxication by different concentrations of either CNF-CD or DNT-CD.

3C: Serum IgG responses to orally administered ovalbumin (OVA). Three groups of 4 mice were fed with OVA alone (control) or co-administered with either CNF-CD (100 μg) or DNT-CD (100 μg). Groups of mice were challenged twice, 2 and 5 weeks after the first immunization and sera collected 30 and 60 days after the first immunization. Levels of the seric anti-OVA IgG titers are expressed as geometric means of the total IgG titers.

Figure 4:
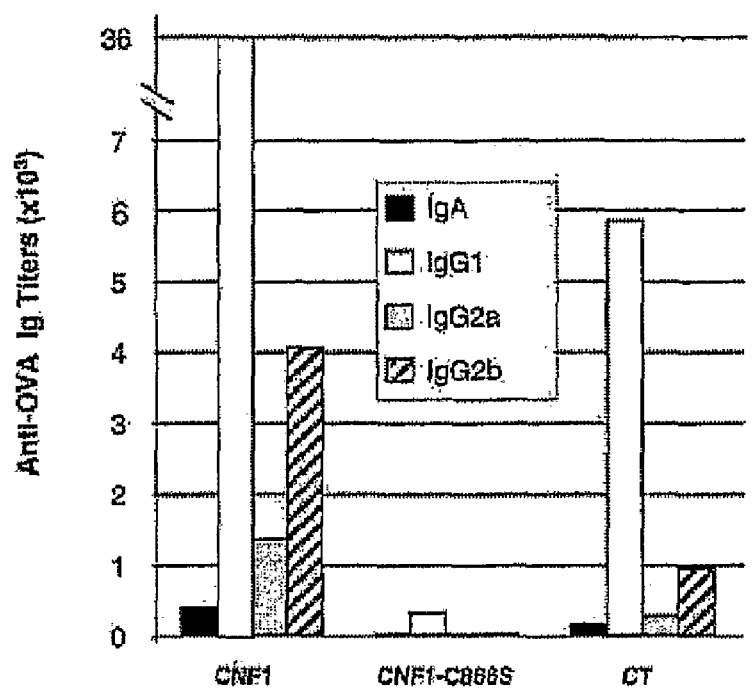

FIG. 4 CNF1, CNF1-C866S and CT Induction of Anti-OVA Ig Subclasses.

Three groups of three mice were challenged twice after the first immunization and sera collected 45 days after the first immunization. Levels of the anti-OVA Ig subclasses are expressed as geometric means (histogram).

Figure 5:
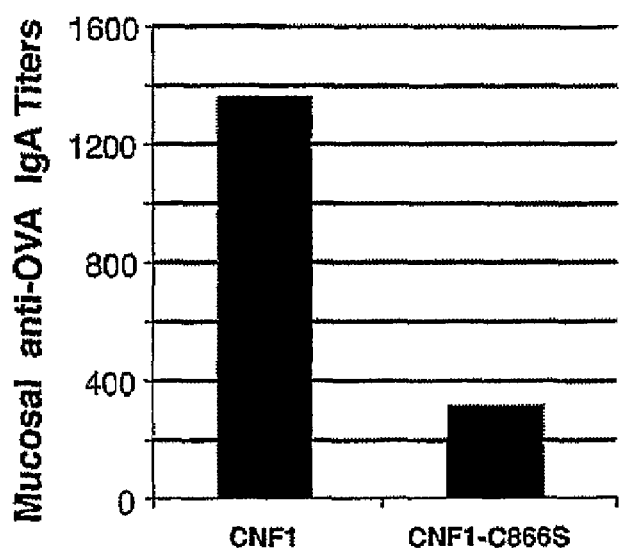

FIG. 5: CNF1 Induction of Mucosal Anti-OVA IgA Response.

Two groups of three mice were challenged twice, after the first immunization, with OVA supplemented with 10 μg of either CNF1 or CNF1-C866S. Mice were processed according to the PERFEXT method (see the section Material and Method). Levels of the anti-OVA IgA responses are expressed as geometric means (histogram).

Figure 6:
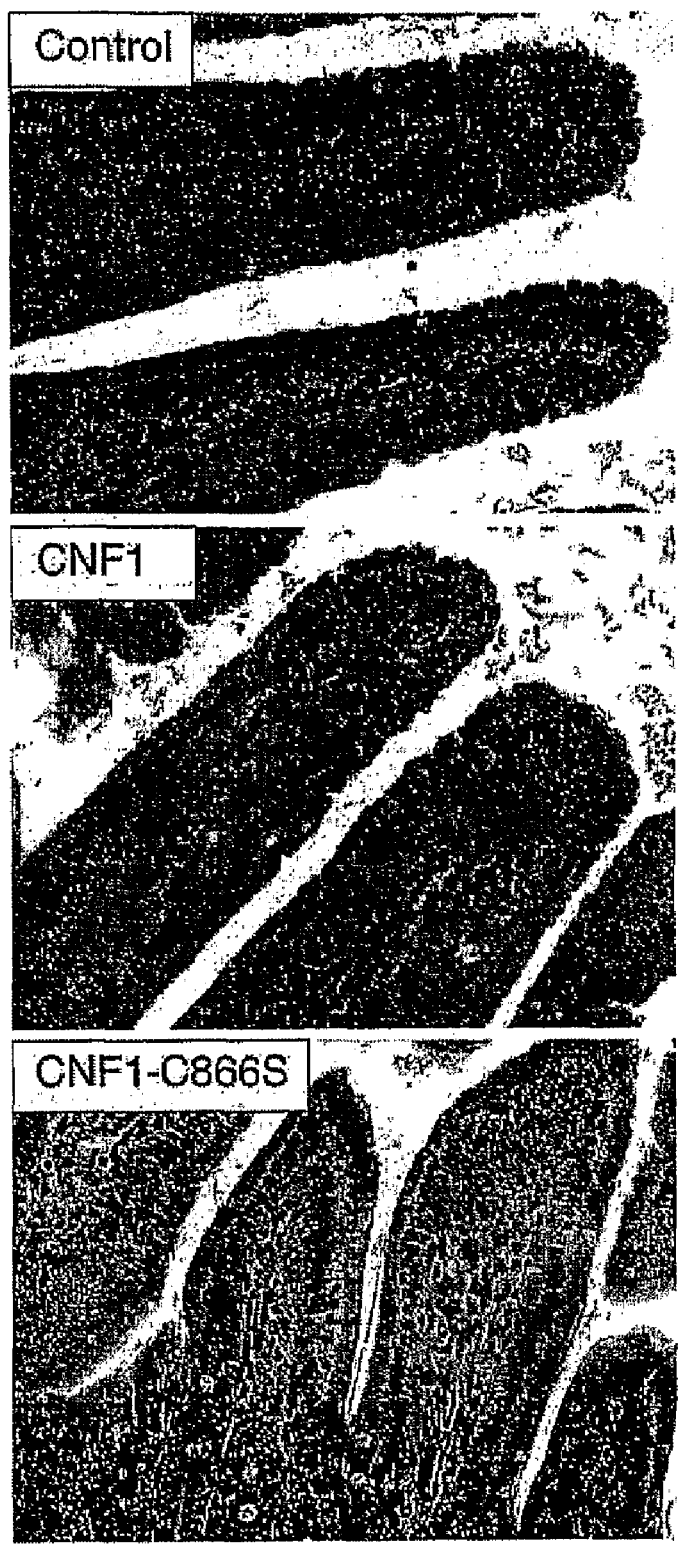

FIG. 6: Histology of Small Intestines of Mice Fed CNF1 or CNF1-C866S as Compared to Control Untreated Mice.

Shown are paraffin sections stained with haematoxylin and eosin.

Figure 7:
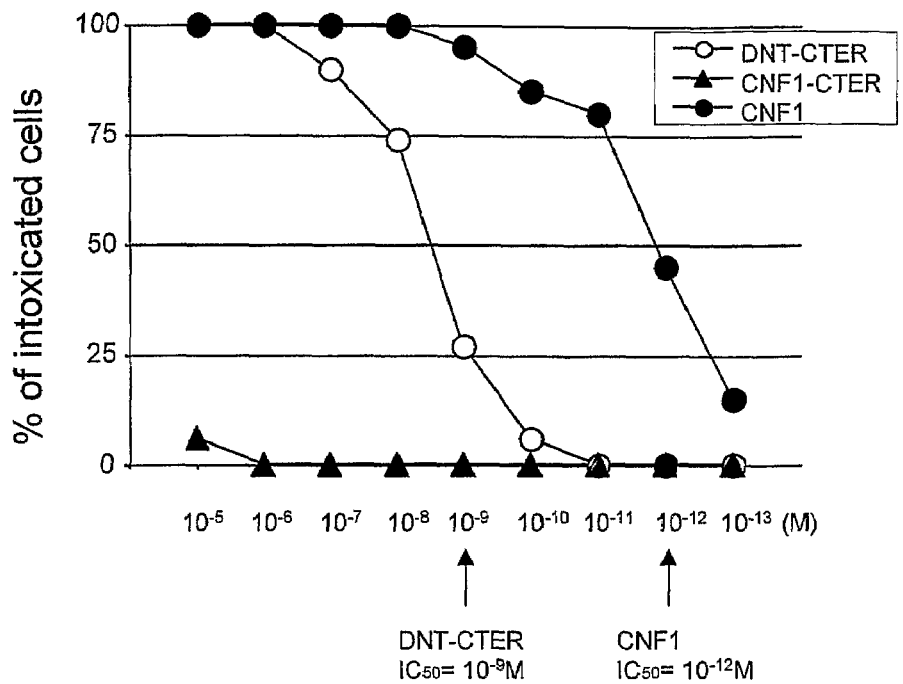
Figure 7:
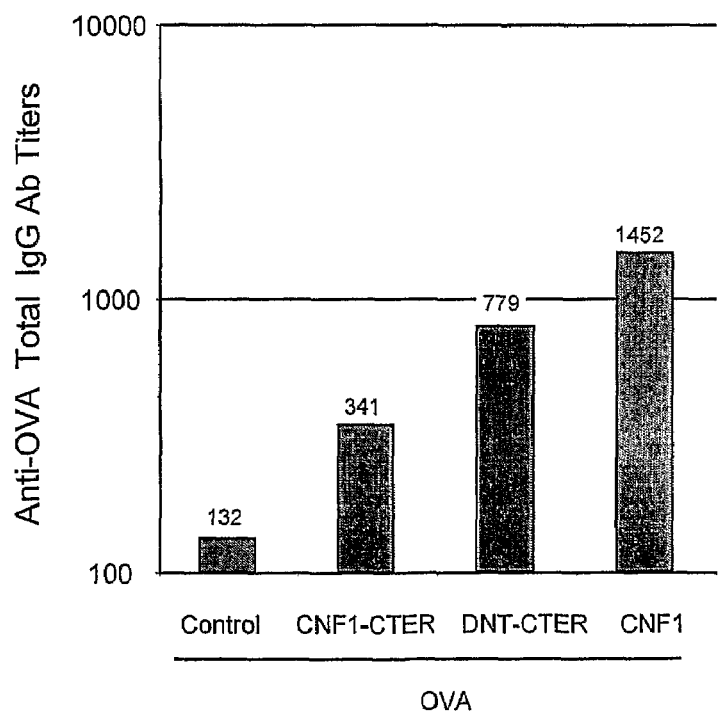

FIG. 7: Measure of the Immunoadjuvant Properties and Toxin Activity of CNF1 and DNT.

7A: Measure of the toxin activity of CNF1, CNF1-CTER (720-1014), DNT-CTER (1154-1451) estimated by HEp-2 cells multinucleation assay, as previously described (Lemichez et al., 1997). As previously reported, CNF1-CTER is poorly active on cells due to its inability to penetrate into the cytosol (Lemichez et al., 1997). DNT-CTER shows a one thousand lower activity, as compared to CNF1.

7B: Serum IgG antibody responses to orally co-administered ovalbumin (OVA) and DNT or CNF1-toxin catalytic domains. Groups of 4 mice were fed OVA alone or co-administered with either CNF1-CTER (720-1014) (100 μg) or DNT-CTER (1154-1451) (100 μg). For CNF1, a group of height mice were fed OVA and CNF1 (10 μg). Mice were challenged once, two weeks after the first immunization and sera collected 30 days after the first immunization. Data are expressed as geometric mean serum IgG anti-OVA Ab titers.

DETAILED DESCRIPTION OF THE INVENTION

The inventors have found according to the invention that Rho GTPase activators bear immunoadjuvant properties in vivo, when co-administered with an antigen, like ovalbumin.

Rho proteins are essential regulatory molecules controlling the actin cytoskeleton organisation and dynamics to accomplish different tasks such as cell polarity, movement, differentiation and phagocytosis (Takai et al., 2001, Etienne-Manneville et al., 2002, Chimini and Chavrier, (2000)). Importance of Rho proteins in physiology is also evidenced by their direct or indirect implication as part of signaling molecules found mutated in human genetic disorders, as well as targets of numerous bacterial virulence factors and toxins (Boettner and Van Aelst, (2002) Boquet and Lemichez, (2003).

Rho proteins interfere with a large variety of signaling pathways controlling gene transcription (Bishop et al., 2000). Among them, a recent report has evidenced the activation of Rac and Cdc42 downstream the Toll-like receptor 2, a gram positive pathogen molecular pattern recognition receptor (PAMP) (Arbibe et al. (2000), Medzhitov et al. (2002).

Also exemplifying the inter-relation between Rho proteins and the host defences is the Rac, Cdc42, VAV and WASP formation of a supra-molecular activation complex (SMAC or "immunological synapse" crucial for lymphocyte activation (Krawczyk et al. 2001).

Many different pathogenic bacteria have evolved virulence factors and toxins aimed at mimicking an activation of Rho GTPase protein family, naturally occurring in eukaryotic cells via specific regulators namely GEF (for guanine nucleotide exchange factors). These cellular GEF consist in domains comprised in large proteins as best described for Dbl (Olson et al., 1996; Schmidt and Hall 2002). Despite their lack of sequence homologies, virulence factors of pathogenic bacteria, for instance SopE and SopE2 from *Salmonella* have a GEF-like activity (Galan et al., 2000). Some other known factors of pathogenic bacteria, namely IpaC from *Shigella* and CagA from *Helicobacter*, activate Rho GTPases by yet uncharacterised molecular mechanisms (Tran Van Nhieu et al., 2000; Boquet and Lemichez 2003). Finally, a group of bacterial toxins comprising CNF1 also activates Rho proteins through a post-traductional modification (Boquet and Lemichez 2003)

According to the invention, the inventors have now surprisingly found that the cytotoxic necrotising factor 1 (CNF1), has immunoadjuvant properties. More precisely, the inventors have found that CNF1 bears immunostimulatory properties toward the systemic and mucosal responses to orally administrated ovalbumin in mice.

Additionally, the inventors have found that a mutant of CNF1, namely CNF1-C866S, a catalytically inactive mutant of CNF1 toward GTPases, in contrast to the wild type toxin, does not stimulate the systemic and mucosal responses to ovalbumin. This result points for Rho GTPases proteins activation being directly involved in the immunostimulatory effects of CNF1.

Supporting this point, the inventors have also found according to the invention that the catalytic domain of CNF1, and the catalytic domain of DNT, another Rho GTPase activator, bear also immunoadjuvant properties in vivo, when co-administered with an antigen, like ovalbumin.

Taken together, these results demonstrate clearly that different Rho GTPases activators, structurally different, have immunoadjuvant properties.

Furthermore, the inventors have found that non neutralizing anti-CNF1 antibodies are naturally found in humans, and that CNF1 activates the Rho GTPase proteins only transiently. Taken together these results demonstrate that CNF1 can be used as an immunoadjuvant compound, deserved of adverse effects such as the toxic effects described for LPS or Cholera Toxin B.

Accordingly, a first object of the invention consists in a vaccine composition comprising an immunoadjuvant compound, wherein said immunoadjuvant compound consists of a Rho GTPase activator.

By "immunoadjuvant" it is herein intended a substance enhancing the immunogenicity of an antigen. By "Rho GTPase activator" it is intended herein a compound, which maintains Rho GTPases in a form bound to GTP. By "Rho GTPases", the one skilled in the art will understand the proteins belonging to the Rho GTPase family, which encompasses RhoA, RhoB, RhoC, Rac1, Rac2 and Cdc42. (Burridge and Wennerberg, 2004).

The level of Rho GTPase bound to GTP can be easily measured by the methods, referred by those skilled in the art as GST-pull down assays and described for RhoA, B and C by Ren et al., 1999 and for Rac1, Rac2 and Cdc42 by Manser et al., 1998. These methods are described in the section Materials and methods.

The invention also concerns a vaccine composition as described below, wherein said immunoadjuvant is selected from the group consisting of:
  a polypeptide comprising the amino acid sequence starting at the amino acid residue 720 and ending at the amino acid residue 1014 of sequence SEQ ID No 1,
  a polypeptide comprising the amino acid sequence starting at the amino acid residue 720 and ending at the amino acid residue 1014 of sequence SEQ ID No 2,
  a polypeptide comprising the amino acid sequence starting at the amino acid residue 720 and ending at the amino acid residue 1014 of sequence SEQ ID No 3,
  a polypeptide comprising the amino acid sequence starting at the amino acid residue 1146 and ending at the amino acid residue 1451 of sequence SEQ ID No 4,
  a polypeptide comprising the amino acid sequence SEQ ID No 5,
  a polypeptide comprising the amino acid sequence SEQ ID No 6,
  a polypeptide comprising the amino acid sequence SEQ ID No 7,
  a polypeptide comprising the amino acid sequence SEQ ID No 8, and
  a polypeptide comprising the amino acid sequence SEQ ID No 9.

A Rho GTPase activator encompasses peptides comprising the amino acid sequence of interest starting at the amino acid residue 720 and ending at the amino acid residue 1014 of sequence SEQ ID No 1 described above, and comprising a N-terminal amino acid sequence, linked to the amino group of the residue 720 of sequence SEQ ID No 1.

Preferably, the N-terminal amino acid sequence has a length up to 800 amino acid residues.

Preferably, the N-terminal amino acid sequence is homologous to a part or to the full length amino acid sequence starting at the amino acid residue 1 and ending at the amino acid residue 719 of CNF1 of SEQ ID No 1.

In such a case, the N-terminal amino acid sequence can comprise substitutions of non-essential amino acid comprised in the sequence starting at the amino acid residue 1 and ending at the amino acid residue 719 of CNF1 of SEQ ID No 1.

A "non essential" amino acid residue is an amino acid residue that can be altered from the wild type sequence of CNF1 without altering the activating properties of Rho GTPases, whereas an "essential" amino acid residue is required for biological activity.

A Rho GTPase activator encompasses also peptides comprising two or more repeated motifs of the sequence 720-1014 of interest. In such a case, said peptide can comprise also an N-Terminal sequence as defined above.

A Rho GTPase activator encompasses also peptides structurally similar to those described above, derived from the catalytic domain of CNF2 of sequence SEQ ID No 2, the catalytic domain of CNF$_y$ of sequence SEQ ID No 3 and the catalytic domain of DNT of sequence SEQ ID No 4.

The use of the catalytic domain of Rho GTPase activator, as described above, is of particular interest. Indeed, as demonstrated in example 6, in the case of CNF1, and DNT, the use of the catalytic domain of these proteins is less toxic for cells than the overall proteins, but is sufficient to confer immunoadjuvanticity.

A Rho GTPase activator encompasses also peptides comprising:
   the amino acid sequence SEQ ID No 5 corresponding to SOPE, or
   the amino acid sequence SEQ ID No 6 corresponding to SOPE2, or
   The amino acid sequence SEQ ID No 7 corresponding to IpaC, or
   the amino acid sequence SEQ ID No 8 corresponding to CagA, or
   the amino acid sequence SEQ ID No 9 corresponding to the GEF sequence of Dbl,
   which include more amino acids, and exhibit at least the same activity towards Rho GTPase activation.

Alternatively, the immunoadjuvant according to the invention is selected from the group consisting of:
   a polypeptide comprising the amino acid sequence SEQ ID No 1,
   a polypeptide comprising the amino acid sequence SEQ ID No 2,
   a polypeptide comprising the amino acid sequence SEQ ID No 3, and
   a polypeptide comprising the amino acid sequence SEQ ID No 4.

Another object of the invention consists in a vaccine composition, wherein said immunoadjuvant compound is a protein comprising a polypeptide consisting of, from the N-terminal end to the C-terminal end, respectively:
   a) the injection domain of a Rho GTPase activator, and
   b) the catalytic domain of a Rho GTPase activator.

By "injection domain of a Rho GTPase activator" it is intended herein, an amino acid sequence allowing the binding and intracellular penetration of a catalytic domain of a Rho GTPase activator.

By "catalytic domain of a Rho GTPase activator" it is intended herein, an amino acid sequence able to activate a Rho GTPase.

The attachment of the injection domain to the catalytic domain above mentioned, to produce a fusion protein may be effected by any means which produces a link between the two constituents, which is sufficiently stable to withstand the conditions used and which does not alter the function of either constituent.

Preferably, the link between them is covalent.

Numerous chemical cross-linking methods are known and potentially applicable for producing the fusion protein. For example, non-specific chemical cross-linking methods, or preferably methods of direct chemical coupling to a functional group, found only once or a few times in one or both of the polypeptides to be cross-linked.

Coupling of the two constituents can also be accomplished via a coupling or conjugating agent. There are several intermolecular cross-linking reagents, which can be used (see, for example, Means, G. E. et al. (1974)). Among these reagents are, for example, N-succinimidyl 3-(2-pyridyidithio)propionate (SPDP) or N,N'-(1,3-phenylene) bismaleimide.

Cross-linking reagents may be homobifunctional, i.e., having two functional groups that undergo the same reaction such as bismaleimidohexane ("BMH").

Alternatively, to solve the problems of protein denaturation and contamination during chemical conjugation, recombinant techniques can be used to covalently attach the polypeptide of interest to the virulence factor, such as by joining the nucleic acid coding for the polypeptide of interest with the nucleic acid sequence coding for the virulence factor and introducing the resulting gene construct into a cell capable of expressing the conjugate.

Recombinant methodologies required to produce a DNA encoding a desired protein are well known and routinely practiced in the art. Laboratory manuals, for example MOLECULAR CLONING: A LABORATORY MANUAL. Cold Spring Harbor Press: Cold Spring Harbor, N.Y. (1989) describes in detail techniques necessary to carry out the required DNA manipulations.

The fusion protein can be produced in recombinant microorganism transformed therewith. In this process, each protein component is preferably linked in the molecular ratio of 1:1 (injection domain:catalytic domain). The aid of an appropriate linker, in order to allow proper folding of each protein molecule can be useful. As a linker, it is preferable to use a peptide consisting of the appropriate number of amino acids to maintain activity of each protein component, such as, a peptide composed of 0 to 20 amino acids, though glycine, (glycine)$_4$ serine, or [(glycine)$_4$ serine]$_2$.

Preferable vectors include any of the well known prokaryotic expression vectors, recombinant baculoviruses, COS cell specific vectors, or yeast-specific expression constructs.

Alternatively, the two separate nucleotide sequences can be expressed in a cell or can be synthesized chemically and subsequently joined, using known techniques. Alternatively, the fusion protein can be synthesized chemically as a single amino acid sequence (i.e., one in which both constituents are present) and, thus, joining is not needed.

Preferably, the injection domain of a Rho GTPase activator is a polypeptide selected from the group consisting of:
   a polypeptide comprising the amino acid sequence starting at the amino acid residue 1 and ending at the amino acid residue 719 of sequence SEQ ID No 1;
   a polypeptide comprising the amino acid sequence starting at the amino acid residue 1 and ending at the amino acid residue 719 of sequence SEQ ID No 2;
   a polypeptide comprising the amino acid sequence starting at the amino acid residue 1 and ending at the amino acid residue 719 of sequence SEQ ID No 3; and
   a polypeptide comprising the amino acid sequence starting at the amino acid residue 1 and ending at the amino acid residue 1145 of sequence SEQ ID No 4.

Preferably, the catalytic domain of a Rho GTPase activator is a polypeptide selected from the group consisting of:
- a polypeptide comprising the amino acid sequence starting at the amino acid residue 720 and ending at the amino acid residue 1014 of sequence SEQ ID No 1,
- a polypeptide comprising the amino acid sequence starting at the amino acid residue 720 and ending at the amino acid residue 1014 of sequence SEQ ID No 2,
- a polypeptide comprising the amino acid sequence starting at the amino acid residue 720 and ending at the amino acid residue 1014 of sequence SEQ ID No 3,
- a polypeptide comprising the amino acid sequence starting at the amino acid residue 1146 and ending at the amino acid residue 1451 of sequence SEQ ID No 4,
- a polypeptide comprising the amino acid sequence SEQ ID No 5,
- a polypeptide comprising the amino acid sequence SEQ ID No 6,
- a polypeptide comprising the amino acid sequence SEQ ID No 7,
- a polypeptide comprising the amino acid sequence SEQ ID No 8, and a polypeptide comprising the amino acid sequence SEQ ID No 9.

The invention concerns also the vaccine composition as described above, further comprising an antigen.

Preferably, the antigen is selected from the group consisting of a hormone, a protein, a drug, an enzyme, a vaccine composition against bacterial, viral, fungal, prion, or parasitic infections, a component produced by microorganisms, inactivated bacterial toxins such as cholera toxin, ST and LT from *Escherichia coli*, tetanus toxin from *Clostridium tetani*, and proteins derived from HIV viruses.

The amount of antigen, and immunoadjuvant compound in the vaccine composition according to the invention, the dosages administered, are determined by techniques well known to those skilled in the pharmaceutical art, taking into consideration such factors as the particular antigen, the age, sex, weight, species, and condition of the particular animal or patient, and the route of administration.

In a preferred embodiment, the vaccine composition according to the invention, further comprises one or more components selected from the group consisting of surfactants, absorption promoters, water absorbing polymers, substances which inhibit enzymatic degradation, alcohols, organic solvents, oils, pH controlling agents, preservatives, osmotic pressure controlling agents, propellants, water and mixture thereof.

The vaccine composition according to the invention can further comprise a pharmaceutically acceptable carrier. The amount of the carrier will depend upon the amounts selected for the other ingredients, the desired concentration of the antigen, the selection of the administration route, oral or parenteral, etc. The carrier can be added to the vaccine at any convenient time. In the case of a lyophilised vaccine, the carrier can, for example, be added immediately prior to administration. Alternatively, the final product can be manufactured with the carrier.

Examples of appropriate carriers include, but are not limited to, sterile water, saline, buffers, phosphate-buffered saline, buffered sodium chloride, vegetable oils, Minimum Essential Medium (MEM), MEM with HEPES buffer, etc.

Optionally, the vaccine composition of the invention may contain conventional, secondary adjuvants in varying amounts depending on the adjuvant and the desired result. The customary amount ranges from about 0.02% to about 20% by weight, depending upon the other ingredients and desired effect.

Examples of suitable secondary adjuvants include, but are not limited to, stabilizers; emulsifiers; aluminum hydroxide; aluminum phosphate; pH adjusters such as sodium hydroxide, hydrochloric acid, etc.; surfactants such as Tween® 80 (polysorbate 80, commercially available from Sigma Chemical Co., St. Louis, Mo.); liposomes; iscom adjuvant; synthetic glycopeptides such as muramyl dipeptides; extenders such as dextran or dextran combinations, for example, with aluminum phosphate; carboxypolymethylene; bacterial cell walls such as mycobacterial cell wall extract; their derivatives such as *Corynebacterium parvum; Propionibacterium acne; Mycobacterium bovis*, for example, Bovine Calmette Guerin (BCG); vaccinia or animal poxvirus proteins; subviral particle adjuvants such as orbivirus; cholera toxin; N,N-dioctadecyl-N',N'-bis(2-hydroxyethyl)-propanediamine (pyridine); monophosphoryl lipid A; dimethyldioctadecylammonium bromide (DDA, commercially available from Kodak, Rochester, N.Y.); synthetics and mixtures thereof. Desirably, aluminum hydroxide is admixed with other secondary adjuvants or an immunoadjuvant such as Quil A.

Examples of suitable stabilizers include, but are not limited to, sucrose, gelatin, peptone, digested protein extracts such as NZ-Amine or NZ-Amine AS. Examples of emulsifiers include, but are not limited to, mineral oil, vegetable oil, peanut oil and other standard, metabolizable, nontoxic oils useful for injectables or intranasal vaccines compositions.

For the purpose of this invention, these adjuvants are identified herein as "secondary" merely to contrast with the above-described immunoadjuvant compound, consisting of a Rho GTPase activator, that is an essential ingredient in the vaccine composition for its effect in combination with an antigenic substance to significantly increase the humoral immune response to the antigenic substance. The secondary adjuvants are primarily included in the vaccine formulation as processing aids although certain adjuvants do possess immunologically enhancing properties to some extent and have a dual purpose.

Conventional preservatives can be added to the vaccine composition in effective amounts ranging from about 0.0001% to about 0.1% by weight. Depending on the preservative employed in the formulation, amounts below or above this range may be useful. Typical preservatives include, for example, potassium sorbate, sodium metabisulfite, phenol, methyl paraben, propyl paraben, thimerosal, etc.

The choice of inactivated, modified or other type of vaccine composition and method of preparation of the improved vaccine composition formulation of the present invention are known or readily determined by those of ordinary skill in the art.

A pharmacologically effective amount of the immunoadjuvant compound according to the invention may be given, for example orally, parenterally or otherwise, concurrently with, sequentially to or shortly after the administration of a an antigenic substance in order to potentiate, accelerate or extend the immunogenicity of the antigen.

While the dosage of the vaccine composition depends upon the antigen, species, body weight of the host vaccinated or to be vaccinated, etc., the dosage of a pharmacologically effective amount of the vaccine composition will usually range from about 50 µg to about 500 µg per dose, per kilogram of body weight, in a mouse model.

Although the amount of the particular antigenic substance in the combination will influence the amount of the immunoadjuvant compound according to the invention, necessary to improve the immune response, it is contemplated that the practitioner can easily adjust the effective dosage amount of the immunoadjuvant compound through routine tests to meet the particular circumstances.

As a general rule, the vaccine composition of the present invention is conveniently administered orally, parenterally (subcutaneously, intramuscularly, intravenously, intradermally or intraperitoneally), intrabuccally, intranasally, or transdermally. The route of administration contemplated by the present invention will depend upon the antigenic substance and the co-formulants. For instance, if the vaccine composition contains saponins, while non-toxic orally or intranasally, care must be taken not to inject the sapogenin glycosides into the blood stream as they function as strong hemolytics. Also, many antigens will not be effective if taken orally. Preferably, the vaccine composition is administered subcutaneously, intramuscularly or intranasally.

The dosage of the vaccine composition will be dependent upon the selected antigen, the route of administration, species, body weight and other standard factors. It is contemplated that a person of ordinary skill in the art can easily and readily titrate the appropriate dosage for an immunogenic response for each antigen to achieve the effective immunizing amount and method of administration.

The inventors have also shown, in example 1 that CNF1 has Immunoadjuvant properties when coadministered orally with an antigen. They have also shown that this coadministration enhances the total IgA antibody titer in mice. This last result is typical of a mucosal response to an immunisation.

Consequently, a further object of the invention is a vaccine composition according to the invention, for administration to a mucosal surface.

This mode of administration presents a great interest. Indeed, the mucosal membranes contain numerous of dendritic cells and Langerhans cells, which are excellent antigen detecting and antigen presenting cells. The mucosal membranes are also connected to lymphoid organs called mucosal associated lymphoid tissue, which are able to forward an immune response to other mucosal areas. An example of such an epithelia is the nasal epithelial membrane, which consists of practically a single layer of epithelial cells (pseudostratified epithelium) and the mucosal membrane in the upper respiratory tract is connected to the two lymphoid tissues, the adenoids and the tonsils. The extensive network of blood capillaries under the nasal mucosal of the high density of B and T cells, are particularly suited to provide a rapid recognition of the antigen and provide a quick immunological response.

Preferably, the mucosal surface is selected from the group consisting of mucosal surfaces of the nose, lungs, mouth, eye, ear, gastrointestinal tract, genital tract, vagina, rectum, and the skin.

Another object of the invention is a vaccine composition for an oral administration.

The invention concerns also a protein comprising a polypeptide consisting of; from the N-terminal end to the C-terminal end, respectively:
a) the injection domain of a Rho GTPase activator as described above, and
b) the catalytic domain of a Rho GTPase activator as described above.

The invention further concerns the use of a polypeptide of interest, for manufacturing a vaccine composition.

The invention also concerns the use of a fusion protein as described above for manufacturing a vaccine composition.

Further details of the invention are illustrated in the following non-limiting examples.

MATERIALS AND METHODS

Cells and Reagents

Human umbilical vein endothelial cells (HUVEC) were obtained from PromoCell (Heidelberg, Germany). Cells were grown in Human Endothelial SFM medium (Invitrogen Co, Paisley, Scotland) supplemented with defined growth factors (d-SFM): 10 ng/ml EGF and 20 ng/ml bFGF (Invitrogen Co), 1 µg/ml heparin (Sigma-Aldrich) and either 20% fetal bovine serum (Invitrogen Co) or 1% (W/V) bovine serum albumin (ELISA grade, Sigma-Aldrich) together with penicillin and streptomycin (Invitrogen Co). Cells were grown on 0.2% gelatine coated dishes (Sigma-Aldrich). Transfections of HUVEC were carried out as described by Mettouchi et al., 2001. Antibodies used were monoclonal anti-β actin antibody [clone AC-74] (Sigma-Aldrich); anti-RhoA, anti-Cdc42, anti-Rac1 and anti-Ras antibodies (Transduction Laboratories); anti-HA [clone 11] (BabCO); anti-E-selectin [clone CTB202] (Santa Cruz Biotechnology) and rabbit polyclonal anti-phospho-p44/42 MAP kinase (Thr202/Tyr204), anti phospho-p38 MAP kinase (Thr180/Tyr182) and anti phospho-c-Jun (Ser73) (Cell Signaling Technology); anti-human IκB-α (Upstate Biotechnology); anti-TRAF1 (H-186, Santa Cruz Biotechnology). Primary antibodies were visualized using goat anti-mouse or anti-rabbit horseradish peroxidase-conjugated secondary antibodies (DAKO, Glostrup, Denmark). TRAF1 rabbit antibodies were visualized using biotin-XX goat anti-rabbit IgG followed by streptavidin horseradish peroxidase conjugate (Molecular Probes). DNA vectors corresponding to pcDNA3RhoQ63L, RacQ61L and Cdc42Q61L were provided by Manor, D. (Lin et al., 1999).

Toxins

Purified CT was obtained from List Biologicals (Campbell, Calif.). CNF1 and CNF1-C866S toxins production and purification were performed as previously described (Munro et al., 2004). Briefly, overnight cultures of *E. coli* OneShot, carrying pCR2cnf1 or pCR2cnf1C866S were lysed in PBS using a French Press. After ammonium sulfate precipitation and dialysis against Tris-NaCl buffer, the soluble fraction was then applied to series of column purifications. Protein purification was followed by SDS-PAGE. The activity of the different batches of CNF1 toxin was estimated by multinucleation assay, as previously described Lemichez et al., 1997). The purified CNF1 toxin used in this study produced, at 10-12 M, 50% of multinucleation of HEp-2 cells after 48 h of exposure. CNF1 catalytic domain (amino acids 720-1014) and DNT catalytic domain (amino acids 1154-1451) were produced using the same methods and activities were assessed as described earlier for CNF1. All protein preparations were found to contain doses of endotoxin below 0.12 EU/ml of FDA Reference Standard, using the Multi-Test *Limulus Amebocyte* Lysate Pyrogen Plus® (Biowhittaker, Walkersville, Md.). Activation and degradation of Rac was assessed using GST-protein pulldown experiment as previously described (Doye et al., 2002).

Immunizations

Females BALB/c mice were purchased from Charles River Laboratories (L'Arbresle, France). They were maintained and handled according to the regulations of the European Union and the French Department of Health. In all experiments, 4-8 week-old female mice were used. Mice were fed either CNF1, CNF1-C866S (a catalytic inactive toxin), catalytic domains of CNF1 (CNF-CD) and DNT (DNT-CD) or CT in the presence or absence of 5 mg of ovalbumin (OVA) (grade V, Sigma-Aldrich, St. Louis, Mo.) dissolved in a solution of 500 µl of 3% NaHCO3. Animals were fed on either two or three consecutive occasions, as detailed in figure legends, 10-12 days apart.

Measurements of Serum Antibody Responses

Serum antibody levels against OVA were determined by means of solid-phase ELISA, as previously described (anjuère et al., 2003). Briefly, serial three-foldilutions of test and control sera were incubated for 2 h at room temperature in OVA-coated polystyrene microtiter wells (Nunc-Immuno™ Plates, MaxiSorp™ Surface, Nunc, Denmark). After washes with PBS containing 0.05% Tween, wells were exposed to 0.1 ml of PBS-Tween containing appropriately diluted HRP-conjugated goat anti-mouse IgG, IgG1, IgG2a, IgG2b and IgA (Southern Biotech Inc., Birmingham, Ala.). Plates were developed with BM blue, POD chromogenic substrate (Roche Applied Science, Indianapolis, Ind.) and monitored spectrophotometrically. Titers were defined as the reciprocal of the highest dilution of serum giving an absorbance value of twice above control, corresponding to pre-immune serum.

Measurements of Mucosal Antibody Responses

Six days after the last immunization, mice were anesthetized with entobarbital and injected with pyrogen-free isotonic saline containing 100 units heparin. The carotid vein was cut and animals were perfused in situ with 25 ml of PBS containing 100 units/ml heparin administered by intracardiac injection to minimize contamination with blood. The small intestines were resectioned, opened longitudinally and washed with PBS. Sections were cut into small fragments and further perfused with PBS-heparin for 4 h at 4° C. Tissue fragments were weighed and then manipulated according to the PERFEXT method, based upon sequential perfusion and detergent extraction (Villavedra et al., 1997). Briefly, fragments were homogenized, suspended in 2 ml of extraction buffer/mg of tissue and incubated overnight at 4° C. The extraction buffer consisted of PBS supplemented with 2% saponin (Sigma) and protease inhibitors (Complete, Boehringer). Samples were then kept frozen at −80° C. until assayed. Thirty minutes before use, specimens were allowed to thaw at room temperature and spun at 16,000×g for 10 min. Supernatants were assayed for IgA and IgG anti-OVA antibody titers as described earlier.

Histology

Mice were fed CNF1 or CNF1-C866S. After 48 h, mice were killed and the small intestines were collected, fixed in formalin and embedded in paraffin wax. Consecutive 5 µm paraffin sections were stained with haematoxylin and eosin.

DNA Array Analysis

HUVEC were seeded at 8 $10^6$ cells/150 mm gelatin-coated dish in d-SFM containing BSA. Cells were intoxicated in parallel for 3 h and 24 h in d-SFM/BSA supplemented with $10^{-9}$M CNF1. Cells were lysed in RTL buffer for total RNA extraction, according to the manufacturer (RNeasy MiniKit, Qiagen). CNF1 regulated genes were analyzed using Affymetrix® Human GeneChip U133A and U133B, by Aros Applied Biotechnology ApS (www.arosab.com), as recommended by the manufacturer (www.Affymetrix.com).

ELISA

HUVEC were seeded 24 h before toxin addition at 2 $10^5$ cells/22.5 mm or 5 $10^5$ cells/35 mm well in d-SFM containing serum. Intoxication of cells was performed by addition of fresh medium containing CNF1, for different periods of time. One hour before intoxication ending the medium was replaced by d-SFM containing BSA for ELISA. IL-8, MCP-1, IL-6, MIP3-α, TNF-α and RANTES production were assessed using human Quantikine® immunoassays, as recommended by the manufacturer (R & D Systems, Abingdon, UK).

Pull-Down and Immunoblotting Detection of Activated-Rho GTPases

Levels of activated-RhoA, -RhoB, -RhoC, -Rac1, -Rac2, -Cdc42 were measured using classical Rho effector pull-down assays developed by Manser et al., 1998 and Ren et al., 1999. For antibodies description see the cells and reagents section.

Briefly, the measure of the levels of activated-RhoA, -B and -C was performed as followed. Cells were lysed in 50 mM Tris, pH7.2, 500 mM NaCl, 10 mM MgCl2, 1% Triton X-100, 0.5% deoxicholate, 0.1% SDS and protease inhibitors. Cell lysates were clarified by centrifugation at 13000 g at 4° C. for 10 min. and equal volumes of lysates (corresponding to 1 mg of total proteins) were incubated with 30 micrograms GST-RBD (Rho binding domain of Rhotekin fused to GST and described in Ren et al., 1999) beads at 4° C. for 45 min. The beads were washed four times with buffer B (50 mM Tris, pH7.2, 500 mM NaCl, 10 mM MgCl2, 1% Triton X-100 and protease inhibitors). Bound Rho proteins were resolved by SDS-PAGE and transferred on PVDF membranes. Activated-Rho proteins were detected by immunoblotting using a monoclonal antibody against either RhoA and RhoC or RhoB and anti-mouse horseradish peroxidase-conjugated secondary antibody followed by chemiluminescence detection.

The measure of the levels of activated-Rac1, Rac2 and Cdc42 was determined, as followed. Cells were lysed in LB buffer (25 mM Tris, pH7.5, 150 mM NaCl, 5 mM MgCl2, 0.5% Triton X-100, 4% glycerol and protease inhibitors). Cell lysates were clarified by centrifugation at 13000 g at 4° C. for 10 min. and equal volumes of lysates (corresponding to 1 mg of total proteins) were incubated with 30 micrograms GST-PAK70-106 (Rac/Cdc42 binding domain of p21 PAK fused to GST and described in Manser et al., 1998) beads at 4° C. for 45 min. The beads were washed four times with LB. Bound Rac and Cdc42 proteins were resolved by SDS-PAGE and transferred on PVDF membranes. Activated-Rac1, 2 or activated-Cdc42 proteins were detected by immunoblotting using a monoclonal antibody against either Rac1, 2 or Cdc42 and anti-mouse horseradish peroxidase-conjugated secondary antibody followed by chemiluminescence detection.

For activated Ras measurements GST-RBD1-149 of Raf1 was used as described by the authors (de Rooij and Bos, 1997).

EXAMPLE 1

CNF1 Effects on Cell Signaling Pathways

Figure 1:
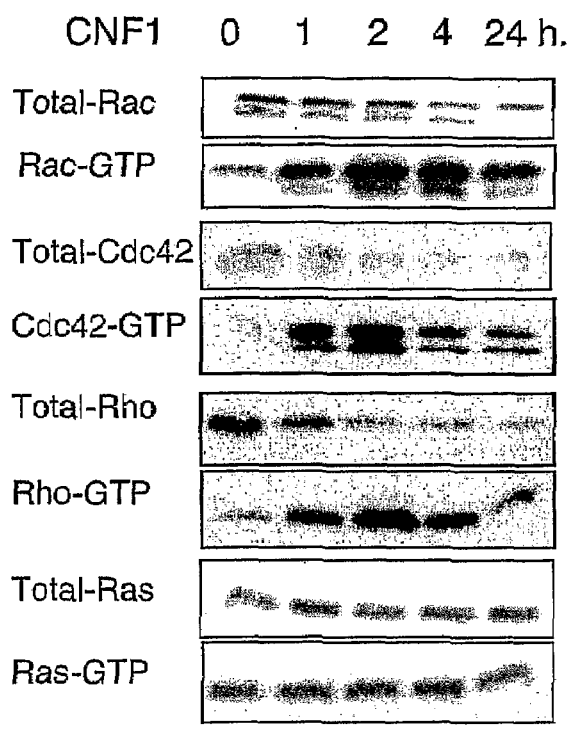
FIG. 1: CNF1 Effects on Cell Signaling Pathway.
Figure 1:
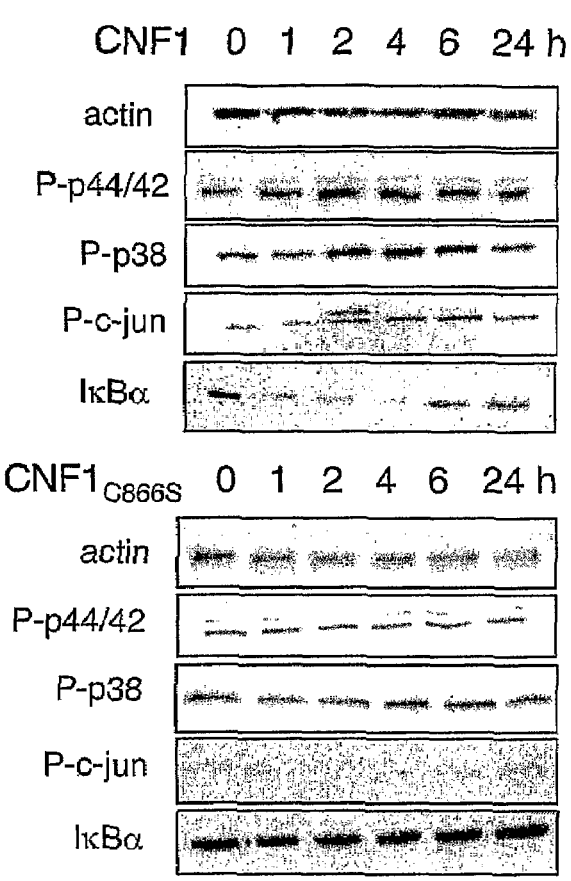
Figure 1:
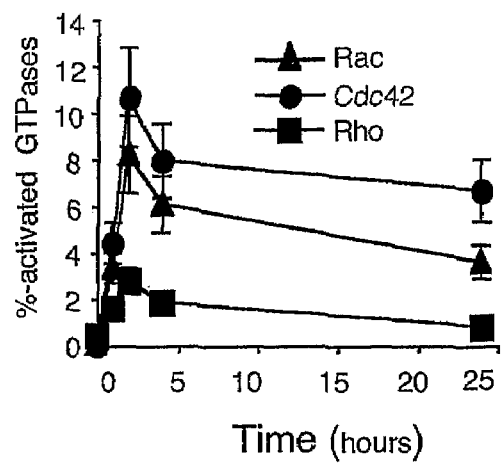

Kinetics of CNF1-induced Rac1, Cdc42 and RhoA activation have been studied. These kinetics show the specificity of Rho protein activation, as compared to the Ras GTPase (FIG. 1A, 1B). Obviously, these measurements do not represent an exhaustive list of the Rho proteins activated by CNF1, other Rho bearing the canonical sequence for CNF1 recognition/modification (Lerm et al., 1999). These measurements rather indicated that all the three Rho proteins exhibited a maximal activation around 2 hours in HUVEC intoxicated with $10^{-9}$M CNF1 (FIG. 1B). CNF1 interference with classical signaling pathways leading to gene regulation, has also been shown. Consistent with the absence of Ras activation measured, CNF1 did not produce ERK1/2 phosphorylation (FIG. 1A, 1C). CNF1 rather appeared to interfere both with the SAP-kinase signaling pathways, unraveled by p38MAP-kinase and cjun phosphorylations. CNF1 also interferes with the NF-kappaB pathway, as shown by IkB depletion (FIG. 1C). Host cells have evolved cell surface receptors to get alarmed of the presence of PAMP (Medzhitov and Janeway, 2002). PAMP receptors initiate an innate immune response through IkB depletion for NFkB activation (Barton and Medzhitov, 2003). That cell treatment with the catalytic inactive CNF1-C866S toxin was devoid of interference with all signaling pathways tested, especially NFkB, strongly suggested an absence of cell recognition of CNF1 as a PAMP (FIG. 1C).

EXAMPLE 2

Serum Anti-OVA Response Following Mucosal Immunization of Mice Co-Fed CNF1

Using a mouse model, characteristics of the host humoral response to CNF1 were investigated. Animals orally immunized with OVA, a prototype soluble antigen, co-administered with CNF1 (10 µg) displayed serum IgG anti-OVA antibody responses (geometric mean titer 7768.7) comparable to those elicited by cholera toxin (geometric mean titer 6450) (FIG. 2). Under these experimental conditions, no serum anti-CNF1 responses were detected (not shown). It was also verified that neither CNF1 nor CT alone elicited production of seric anti-OVA IgG antibodies (not shown). Immunization with a lower dose of CNF1 (1 µg) had negligible effects on serum anti-OVA responses when compared to control animals (geometric mean titers 868.7 and 787.5, respectively) (FIG. 2). Finally, immunization with 10 µg of the catalytic inactive CNF1 mutant (CNF1-C866S) failed to enhance serum anti-OVA responses in animals co-fed OVA (FIG. 2). This result together with the fact that both CNF1 and CNF1-C866S were purified using identical conditions, excludes a possible stimulation of the IgG anti-OVA antibody responses by factors co-purified with CNF1. Collectively, these results show that the anti-OVA response elicited by CNF1 is dose dependent and requires its catalytic activity. As described for CNF1 (Doye et al., 2002), the catalytic domain of the closely related toxin DNT (DNT-CD) produced a transient activation of Rac due to the cellular depletion of this GTPase (FIG. 3A). Effects of DNT-CD were quantified using a classical HEp-2 cell assay, which gives a 50% multinucleation of cells at 10-12M CNF1 (Lemichez et al., 1997). In contrast to DNT-CD, which showed a 50% effect at 10-9 M, the CNF1 catalytic domain CNF-CD had negligible effects (FIG. 3B). When immunostimulatory effects of both catalytic domains CNF-CD and DNT-CD are compared, only mice immunized with 100 µg of DNT-CD developed a significant level of serum IgG anti-OVA antibodies (DNT-CD geometric mean titer of 7015 at 60 days) (FIG. 3C).

EXAMPLE 3

Serum Antibody Isotype Responses

Sera from mice immunized with OVA together with 10 µg of CNF1, CNF1-C866S or CT were then tested for the presence of anti-OVA IgA and IgG subclasses. The isotype distribution of Ig anti-OVA antibody responses in animals immunized with CNF1 was similar to that observed in animals immunized with CT and was mainly accounted for by IgG1 and IgG2b. Likewise, mice fed a mixture of OVA and CNF1-C866S had no detectable anti-OVA antibody responses in any isotype (FIG. 4). Taken together, these results indicate that CNF1, when given orally with OVA, promotes systemic anti-OVA responses with a profile of IgG subclasses similar to that induced by cholera toxin.

EXAMPLE 4

Mucosal IgA Antibody Response

Using the PERFEXT method, we then evaluated the ability of CNF1 to potentiate mucosal antibody responses in animals orally immunized with OVA. Sections of small intestine collected from groups of mice orally immunized with OVA, given together with CNF1 or CNF1-C866S, were analyzed for IgA content 2 weeks after the last of three immunizations. As illustrated in FIG. 5, oral co-administration of OVA with CNF1 elicited an antigen specific mucosal IgA response. Mice orally immunized with OVA given alone or admixed with the catalytic inactive CNF1-C866S had no detectable intestinal IgA antibody responses to OVA (FIG. 5).

EXAMPLE 5

Histological Analysis of CNF1 Effects on Small Intestines

Histological analyses of sections of small intestines prepared from mice immunized with CNF1 or CNF1-C866S showed no significant differences to those from control (bicarbonate fed) animals (FIG. 6).

EXAMPLE 6

The Catalytic Domain of DNT Remains Active on Cells and is Sufficient to Confer Adjuvanticity CNF1 belongs to a family of toxins among them DNT, having similar catalytic activity (Boquet and Lemichez 2003). It is shown on FIG. 3A that the catalytic domain of DNT (DNT-CTER) remains active on cells, although showing a lower intoxication property as compared to CNF1. Despite its inability to intoxicate cells (FIG. 7A), the catalytic domain of CNF1 (CNF1-CTER) upon mechanical injection into cells produces a bona fide toxic phenotype (Lemichez et al., 1997). It has been taken advantage of the above observations to test the adjuvant properties of the catalytic domains of both toxins. Mice were fed 10 times higher quantities of both toxin catalytic domains, as compared to CNF1. In these conditions it has been observed that DNT-CTER stimulated significantly the anti-OVA IgG responses (FIG. 7B). CNF1-CTER also produced a stimulation of the anti-OVA IgG responses, although at a lower level (FIG. 7B). Taken together, these results indicate that the adjuvanticity of this group of toxin is encompassed in their catalytic domain. Nevertheless, the injection domain of CNF1-toxin together with its catalytic domain, allows the use of lower doses to induce a significantly higher biological effect.

REFERENCES

Anjuère, F., George-Chandy, A., Audant, F., Rousseau, D., Holmgren J., and Czerkinsky, C. (2003). Transcutaneous immunization with cholera toxin B subunit adjuvant suppresses IgE antibody responses via selective induction of Th1 immune responses. J. Immunol. 170, 1586-1592.

Arbibe, L., Mira, J. P., Teusch, N., Kline, L., Guha, M., Mackman, N., Godowski, P. J., Ulevitch, R. J., and Knaus, U. G. (2000). Toll-like receptor 2-mediated NF-kappa B activation requires a Rac1-dependent pathway. Nat. Immunol. 1, 533-540.

Baggiolini, M., and Loetscher, P. (2000). Chemokines in inflammation and immunity. Immunol. Today 21, 418-420.

Barbieri J. T., Riese M. J., Aktories, K. (2002). Bacterial toxins that modify the actin cytoskeleton. Annu. Rev. Cell. Dev. Biol. 18, 315-344.

Barnhart, B. C., and Peter, M. E. (2003). The TNF receptor 1: a split personality complex. Cell 114, 148-150.

Barton, G. M. and Medzhitov, R. (2003). Toll-like receptor signaling pathways. Science 300, 1524-1525.

Bishop, A. L., and Hall, A. (2000). Rho GTPases and their effector proteins. Biochem. J. 348, 241-255.

Boquet, P., and Lemichez, E. (2003). Bacterial virulence factors targeting Rho GTPases: parasitism or symbiosis? Trends Cell Biol. 13, 238-246.

Burridge, K., and Wennerberg, K. (2004). Rho and Rac take center stage. Cell 116, 167-179

Chimini, G., and Chavrier, P. (2000). Function of Rho family proteins in actin dynamics during phagocytosis and engulfment. Nat. Cell Biol. 2, 191-196.

Dieu, M. C., Vanbervliet, B., Vicari, A., Bridon, J. M., Oldham, E., Ait-Yahia, S., Briere, F., Zlotnik, A., Lebecque, S., and Caux, C. (1998). Selective recruitment of immature and mature dendritic cells by distinct chemokines expressed in different anatomic sites. J. Exp. Med. 188, 373-386.

Doye, A., Mettouchi, A., Bossis, G., Clement, R., Buisson-Touati, C., Flatau, G., Gagnoux, L., Piechaczyk, M., Boquet, P., and Lemichez, E. (2002). CNF1 exploits the ubiquitinproteasome machinery to restrict Rho GTPase activation for bacterial host cell invasion. Cell 111, 553-564.

De Rooij, J., and Bos, J. L. (1997). Minimal Ras-binding domain of Raf1 can be used as an activation-specific probe for Ras. Oncogene 14, 623-625.

Etienne-Manneville, S., and Hall, A. (2002). Rho GTPases in cell biology. Nature 420, 629-635.

Flatau, G., Lemichez, E., Gauthier, M., Chardin, P., Paris, S., Fiorentini, C., and Boquet, P. (1997). Toxin-induced activation of the G protein p21 Rho by deamidation of glutamine. Nature 387, 729-733.

Galan, J. E., and Zhou, D. (2000). Striking a balance: modulation of the actin cytoskeleton by Salmonella. Proc. Natl. Acad. Sci. USA 97, 8754-8761.

Garrett, W. S., Chen, L. M., Kroschewski, R., Ebersold, M., Turley, S., Trombetta, S., Galan, J. E. and Mellman, I. (2000). Developmental control of endocytosis in dendritic cells by Cdc42. Cell 102, 325-334.

Holmgren, J., Czerkinsky, C., Eriksson, K. and Mharandi, A. (2003). Mucosal immunisation and adjuvants: a brief overview of recent advances and challenges. Vaccine 21, S89-95.

Izadpanah, A., Dwinell, M. B., Eckmann, L., Varki, N. M., and Kagnoff, M. F. (2001). Regulated MIP-3alpha/CCL20 production by human intestinal epithelium: mechanism for modulating mucosal immunity. Am. J. Physiol. Gastrointest. Liver Physiol. 280, 710-719.

Janeway, C. A. Jr. (2001). How the immune system works to protect the host from infection: a personal view. Proc. Natl. Acad. Sci. USA. 98, 7461-7468.

Khan, N. A., Wang, Y., Kim, K. J., Chung, J. W., Wass, C. A., and Kim, K. S. (2002). Cytotoxic necrotizing factor-1 contributes to Escherichia coli K1 invasion of the central nervous system J. Biol. Chem. 277, 15607-15612.

Klein, S., de Fougerolles, A. R., Blaikie, P., Khan, L., Pepe, A., Green, C. D., Koteliansky, V., and Giancotti, F. G. (2002). Alpha 5 beta 1 integrin activates an NF-kappa B-dependent program of gene expression important for angiogenesis and inflammation. Mol. Cell. Biol. 22, 5912-5922.

Krawczyk, C., and Penninger, J. M. (2001). Molecular controls of antigen receptor clustering and autoimmunity. Trends Cell Biol. 11, 212-220.

Kubori, T, and Galan, J. E. (2003). Temporal regulation of salmonella virulence effector function by proteasome-dependent protein degradation. Cell 115, 333-342.

Lemichez, E., Flatau, G., Bruzzone, M., Boquet, P., and Gauthier, M. (1997). Molecular localization of the Escherichia coli cytotoxic necrotizing factor CNF1 cell-binding and catalytic domains. Mol. Microbiol. 24, 1061-1070.

Lerm, M., Schmidt, G., Goehring, U. M., Schirmer, J., and Aktories, K. (1999). Identification of the region of rho involved in substrate recognition by Escherichia coli cytotoxic necrotizing factor 1 (CNF1). J. Biol. Chem. 274, 28999-9004.

Lin, R., Cerione, R. A., and Manor, D. (1999). Specific contributions of the small GTPases Rho, Rac, and Cdc42 to Dbl transformation. J. Biol. Chem. 274, 23633-23641.

Manser, E., Loo, T. H., Koh, C. G., et al., (1998) PAK kinases are directly coupled to the PIX family of nucleotide exchange factors. Mol. Cell vol 1 pp 183-192.

Means, G. E. and Feeney, R. E., (1974) Chemical Modification of Proteins, Holden-Day, pp. 39-43

Medzhitov, R., and Janeway, C. A. (2002). Decoding the patterns of self and nonself by the innate immune system. Science 296, 298-300.

Mettouchi, A., Klein, S., Guo, W., Lopez-Lago, M., Lemichez, E., Westwick, J. K., and Giancotti, F. G. (2001). Integrin-specific activation of Rac controls progression through the G(1) phase of the cell cycle. Mol. Cell. 8, 115-127.

Munro P, Flatau G, Doye A, Boyer L, Oregioni O, Mege J L, et al. Activation and proteasomal degradation of Rho GTPases by CNF1 elicit a controlled inflammatory response. J Biol Chem 2004; 279:35849-57.

Mysorekar, I. U., Mulvey, M. A., Hultgren, S. J., and Gordon, J. I. (2002). Molecular regulation of urothelial renewal and host defenses during infection with uropathogenic Escherichia coli. J. Biol. Chem. 277, 7412-7419.

Olson, M. F., Pasteris, N. G., Gorski, J. L. and Hall A. (1996). Faciogenital dysplasia protein (FDG1) and Vav, two related proteins required for normal embryonic development, are upstream regulators of Rho GTPases. Curr Biol. 6, 1628-1633.

Pedron, T., Thibault, C., and Sansonetti, P. J. (2003). The invasive phenotype of Shigella flexneri directs a distinct gene expression pattern in the human intestinal epithelial cell line Caco-2. J. Biol. Chem. 278, 33878-33886.

Powrie F., and Maloy, K. J. (2003). Immunology. Regulating the regulators. Science 299, 1030-1031.

Ren X. D., Kiosses W. B., and Schwartz M. A., (1999) Regulation of the small GTP-binding protein Rho by cell adhesion and the cytoskeleton. EMBO J. vol 18 pp 578-595

Shapiro, S. D. (2003). Immunology: Mobilizing the army. Nature 421, 223-224.

Schmidt, G., Sehr, P., Wilm, M., Seizer, J., Mann, M., and Aktories, K. (1997). Gin 63 of Rho is deamidated by Escherichia coli cytotoxic necrotizing factor-1. Nature 387, 725-729.

Schmidt, A., and Hall, A. (2002). Guanine nucleotide exchange factors for Rho GTPases; turning on the switch. Genes Dev. 16, 1587-1609.

Szyperski, T., Fernandez, C., Mumenthaler, C., and Wuthrich, K. (1998). Structure comparison of human glioma pathogenesis-related protein GliPR and the plant pathogenesis-related protein P14a indicates a functional link between the human immune system and a plant defense system. Proc. Natl. Acad. Sci. USA 95, 2262-2266.

Takai, Y., Sasaki, T., and Matozaki, T. (2001). Small GTP-binding proteins. Physiol. Rev. 81, 153-208.

Tran Van Nhieu, G., Bourdet-Sicard, R., Dumenil, G., Blocker, A., and Sansonetti, P. J. (2000). Bacterial signals and cell responses during *Shigella* entry into epithelial cells. Cell Microbiol. 2, 187-193.

Villavedra, M., Carol, H., Hjulstrom, M., Holmgren, J., and Czerkinsky, C. (1997). "PERFEXT": a direct method for quantitative assessment of cytokine production in vivo at the local level. Res. Immunol. 148, 257-266.

Walmsley, M. J., Ooi, S. K., Reynolds, L. F., Smith, S. H., Ruf, S., Mathiot, A., Vanes, L., Williams, D. A., Cancro, M. P., and Tybulewicz, V. L. (2003). Critical roles for Rac1 and Rac2 GTPases in B cell development and signaling. Science 302:459-462.

Wang, Y., Bjes, E. S., and Esser, A. F. (2000). Molecular aspects of complement-mediated bacterial killing. Periplasmic conversion of C9 from a protoxin to a toxin. J. Biol. Chem. 275, 4687-4692.

Wojciak-Stothard, B., Williams, L., and Ridley, A. J. (1999). Monocyte adhesion and spreading on human endothelial cells is dependent on Rho-regulated receptor clustering. J. Cell Biol. 145, 1293-1307.

Yang, D., Chen, Q., Hoover, D. M., Staley, P., Tucker, K. D., Lubkowski, J., and Oppenheim, J. J. (2003). Many chemokines including CCL20/MIP-3alpha display antimicrobial activity. J. Leukoc. Biol. 74, 448-455.

The invention claimed is:

1. A vaccine composition comprising (a) an antigen and (b) an immunoadjuvant wherein said immunoadjuvant compound consists of a Rho GTPase activator selected from the group consisting of:
   a polypeptide consisting of the amino acid sequence starting at the amino acid residue 720 and ending at the amino acid residue 1014 of sequence SEQ ID NO 1 and
   a polypeptide consisting of the amino acid sequence starting at the amino acid residue 1146 and ending at the amino acid residue 1451 of sequence SEQ ID NO 4.

2. The vaccine composition according to claim 1 wherein said immunoadjuvant compound is selected from the group consisting of:
   the cytotoxic necrotizing factor 1 (CNF1) of SEQ ID NO 1 and
   the dermonecrotic toxin (DNT) of SEQ ID NO 4.

3. The vaccine composition according any one of claims 1 and 2 wherein the antigen is selected from the group consisting of a hormone, a protein, a drug, an enzyme, a vaccine composition against bacterial, viral, fungal, prion, or parasitic infections, a component produced by microorganisms, inactivated bacterial toxins such as cholera toxin, ST and LT from *Escherichia coli* and tetanus toxin from *Clostridium tetani*.

4. The vaccine composition according any one of claims 1 and 2 for administration to a mucosal surface.

5. The vaccine composition according any one of claims 1 and 2 an oral administration.

6. A method for preparing a vaccine composition according to claim 1, comprising the step of:
   adding an immunoadjuvant to an excipient, wherein
   said immunoadjuvant consists of a Rho GTPase activator selected from the group consisting of:
   a polypeptide consisting of the amino acid sequence starting at the amino acid residue 720 and ending at the amino acid residue 1014 of sequence SEQ ID NO 1 and
   a polypeptide consisting of the amino acid sequence starting at the amino acid residue 1146 and ending at the amino acid residue 1451 of sequence SEQ ID NO 4.

7. A method for preparing a vaccine composition according to claim 2, comprising the step of:
   adding an immunoadjuvant to an excipient, wherein
   said immunoadjuvant compound is selected from the group consisting of: the cytotoxic necrotizing factor 1 (CNF1) of SEQ ID NO 1 and the dermonecrotic toxin (DNT) of SEQ ID NO 4.

* * * * *

SEQUENCE LISTING

<160> NUMBER OF SEQ ID NOS: 9

<210> SEQ ID NO 1
<211> LENGTH: 1014
<212> TYPE: PRT
<213> ORGANISM: Escherichia coli

<400> SEQUENCE: 1

```
Met Gly Asn Gln Trp Gln Gln Lys Tyr Leu Leu Glu Tyr Asn Glu Leu
1               5                   10                  15

Val Ser Asn Phe Pro Ser Pro Glu Arg Val Val Ser Asp Tyr Ile Lys
            20                  25                  30

Asn Cys Phe Lys Thr Asp Leu Pro Trp Phe Ser Arg Ile Asp Pro Asp
        35                  40                  45

Asn Ala Tyr Phe Ile Cys Phe Ser Gln Asn Arg Ser Asn Ser Arg Ser
    50                  55                  60

Tyr Thr Gly Trp Asp His Leu Gly Lys Tyr Lys Thr Glu Val Leu Thr
65                  70                  75                  80

Leu Thr Gln Ala Ala Leu Ile Asn Ile Gly Tyr Arg Phe Asp Val Phe
                85                  90                  95

Asp Asp Ala Asn Ser Ser Thr Gly Ile Tyr Lys Thr Lys Ser Ala Asp
            100                 105                 110

Val Phe Asn Glu Glu Asn Glu Glu Lys Met Leu Pro Ser Glu Tyr Leu
        115                 120                 125

His Phe Leu Gln Lys Cys Asp Phe Ala Gly Val Tyr Gly Lys Thr Leu
    130                 135                 140

Ser Asp Tyr Trp Ser Lys Tyr Tyr Asp Lys Phe Lys Leu Leu Leu Lys
145                 150                 155                 160

Asn Tyr Tyr Ile Ser Ser Ala Leu Tyr Leu Tyr Lys Asn Gly Glu Leu
                165                 170                 175

Asp Glu Arg Glu Tyr Asn Phe Ser Met Asn Ala Leu Asn Arg Ser Asp
            180                 185                 190

Asn Ile Ser Leu Leu Phe Phe Asp Ile Tyr Gly Tyr Ala Ser Asp
        195                 200                 205

Ile Phe Val Ala Lys Asn Asn Asp Lys Val Met Leu Phe Ile Pro Gly
    210                 215                 220

Ala Lys Lys Pro Phe Leu Phe Lys Lys Asn Ile Ala Asp Leu Arg Leu
225                 230                 235                 240

Thr Leu Lys Glu Leu Ile Lys Asp Ser Asp Lys Gln Gln Leu Leu Ser
                245                 250                 255
```

-continued

```
Gln His Phe Ser Leu Tyr Ser Arg Gln Asp Gly Val Ser Tyr Ala Gly
        260                 265                 270

Val Asn Ser Val Leu His Ala Ile Glu Asn Asp Gly Asn Phe Asn Glu
        275                 280                 285

Ser Tyr Phe Leu Tyr Ser Asn Lys Thr Leu Ser Asn Lys Asp Val Phe
        290                 295                 300

Asp Ala Ile Ala Ile Ser Val Lys Lys Arg Ser Phe Ser Asp Gly Asp
305                 310                 315                 320

Ile Val Ile Lys Ser Asn Ser Glu Ala Gln Arg Asp Tyr Ala Leu Thr
                325                 330                 335

Ile Leu Gln Thr Ile Leu Ser Met Thr Pro Ile Phe Asp Ile Val Val
        340                 345                 350

Pro Glu Val Ser Val Pro Leu Gly Leu Gly Ile Ile Thr Ser Ser Met
        355                 360                 365

Gly Ile Ser Phe Asp Gln Leu Ile Asn Gly Asp Thr Tyr Glu Glu Arg
        370                 375                 380

Arg Ser Ala Ile Pro Gly Leu Ala Thr Asn Ala Val Leu Leu Gly Leu
385                 390                 395                 400

Ser Phe Ala Ile Pro Leu Leu Ile Ser Lys Ala Gly Ile Asn Gln Glu
                405                 410                 415

Val Leu Ser Ser Val Ile Asn Asn Glu Gly Arg Thr Leu Asn Glu Thr
        420                 425                 430

Asn Ile Asp Ile Phe Leu Lys Glu Tyr Gly Ile Ala Glu Asp Ser Ile
        435                 440                 445

Ser Ser Thr Asn Leu Leu Asp Val Lys Leu Lys Ser Ser Gly Gln His
        450                 455                 460

Val Asn Ile Val Lys Leu Ser Asp Glu Asp Asn Gln Ile Val Ala Val
465                 470                 475                 480

Lys Gly Ser Ser Leu Ser Gly Ile Tyr Tyr Glu Val Asp Ile Glu Thr
                485                 490                 495

Gly Tyr Glu Ile Leu Ser Arg Arg Ile Tyr Arg Thr Glu Tyr Asn Asn
        500                 505                 510

Glu Ile Leu Trp Thr Arg Gly Gly Gly Leu Lys Gly Gly Gln Pro Phe
        515                 520                 525

Asp Phe Glu Ser Leu Asn Ile Pro Val Phe Phe Lys Asp Glu Pro Tyr
        530                 535                 540

Ser Ala Val Thr Gly Ser Pro Leu Ser Phe Ile Asn Asp Asp Ser Ser
545                 550                 555                 560

Leu Leu Tyr Pro Asp Thr Asn Pro Lys Leu Pro Gln Pro Thr Ser Glu
                565                 570                 575

Met Asp Ile Val Asn Tyr Val Lys Gly Ser Gly Ser Phe Gly Asp Arg
        580                 585                 590

Phe Val Thr Leu Met Arg Gly Ala Thr Glu Glu Ala Trp Asn Ile
        595                 600                 605

Ala Ser Tyr His Thr Ala Gly Gly Ser Thr Glu Glu Leu His Glu Ile
        610                 615                 620

Leu Leu Gly Gln Gly Pro Gln Ser Ser Leu Gly Phe Thr Glu Tyr Thr
625                 630                 635                 640

Ser Asn Val Asn Ser Ala Asp Ala Ala Ser Arg Arg His Phe Leu Val
                645                 650                 655

Val Ile Lys Val His Val Lys Tyr Ile Thr Asn Asn Asn Val Ser Tyr
        660                 665                 670
```

```
Val Asn His Trp Ala Ile Pro Asp Glu Ala Pro Val Glu Val Leu Ala
            675                 680                 685

Val Val Asp Arg Arg Phe Asn Phe Pro Glu Pro Ser Thr Pro Pro Asp
        690                 695                 700

Ile Ser Thr Ile Arg Lys Leu Leu Ser Leu Arg Tyr Phe Lys Glu Ser
705                 710                 715                 720

Ile Glu Ser Thr Ser Lys Ser Asn Phe Gln Lys Leu Ser Arg Gly Asn
                725                 730                 735

Ile Asp Val Leu Lys Gly Arg Gly Ser Ile Ser Ser Thr Arg Gln Arg
            740                 745                 750

Ala Ile Tyr Pro Tyr Phe Glu Ala Ala Asn Ala Asp Glu Gln Gln Pro
        755                 760                 765

Leu Phe Phe Tyr Ile Lys Lys Asp Arg Phe Asp Asn His Gly Tyr Asp
    770                 775                 780

Gln Tyr Phe Tyr Asp Asn Thr Val Gly Leu Asn Gly Ile Pro Thr Leu
785                 790                 795                 800

Asn Thr Tyr Thr Gly Glu Ile Pro Ser Asp Ser Ser Leu Gly Ser
                805                 810                 815

Thr Tyr Trp Lys Lys Tyr Asn Leu Thr Asn Glu Thr Ser Ile Ile Arg
            820                 825                 830

Val Ser Asn Ser Ala Arg Gly Ala Asn Gly Ile Lys Ile Ala Leu Glu
        835                 840                 845

Glu Val Gln Glu Gly Lys Pro Val Ile Ile Thr Ser Gly Asn Leu Ser
    850                 855                 860

Gly Cys Thr Thr Ile Val Ala Arg Lys Glu Gly Tyr Ile Tyr Lys Val
865                 870                 875                 880

His Thr Gly Thr Thr Lys Ser Leu Ala Gly Phe Thr Ser Thr Thr Gly
                885                 890                 895

Val Lys Lys Ala Val Glu Val Leu Glu Leu Leu Thr Lys Glu Pro Ile
            900                 905                 910

Pro Arg Val Glu Gly Ile Met Ser Asn Asp Phe Leu Val Asp Tyr Leu
        915                 920                 925

Ser Glu Asn Phe Glu Asp Ser Leu Ile Thr Tyr Ser Ser Ser Glu Lys
    930                 935                 940

Lys Pro Asp Ser Gln Ile Thr Ile Ile Arg Asp Asn Val Ser Val Phe
945                 950                 955                 960

Pro Tyr Phe Leu Asp Asn Ile Pro Glu His Gly Phe Gly Thr Ser Ala
                965                 970                 975

Thr Val Leu Val Arg Val Asp Gly Asn Val Val Arg Ser Leu Ser
            980                 985                 990

Glu Ser Tyr Ser Leu Asn Ala Asp Ala Ser Glu Ile Ser Val Leu Lys
        995                 1000                1005

Val Phe Ser Lys Lys Phe
    1010

<210> SEQ ID NO 2
<211> LENGTH: 1014
<212> TYPE: PRT
<213> ORGANISM: Escherichia coli

<400> SEQUENCE: 2

Met Asn Val Gln Trp Gln Gln Lys Tyr Leu Leu Glu Tyr Asn Glu Leu
  1               5                  10                  15

Val Ser Asn Phe Pro Ser Pro Glu Arg Val Val Ser Asp Tyr Ile Arg
             20                  25                  30
```

-continued

```
Arg Cys Phe Lys Thr Asp Leu Pro Trp Phe Ser Gln Val Asp Pro Asp
            35                  40                  45

Asn Thr Tyr Phe Ile Arg Phe Ser Gln Ser Arg Ser Asn Ser Arg Ser
    50                  55                  60

Tyr Thr Gly Trp Asp His Leu Gly Lys Tyr Lys Thr Gly Val Leu Thr
65                  70                  75                  80

Leu Thr Gln Ala Ala Leu Ile Asn Ile Gly Tyr His Phe Asp Val Phe
                85                  90                  95

Asp Asp Ala Asn Ala Ser Ala Gly Ile Tyr Lys Thr Ser Ser Ala Asp
            100                 105                 110

Met Phe Asn Glu Lys Asn Glu Glu Lys Met Leu Pro Ser Glu Tyr Leu
        115                 120                 125

Tyr Phe Leu Lys Gly Cys Asp Phe Ser Gly Ile Tyr Gly Arg Phe Leu
    130                 135                 140

Ser Asp Tyr Trp Ser Lys Tyr Asp Lys Phe Lys Leu Leu Leu Lys
145                 150                 155                 160

Asn Tyr Tyr Ile Ser Ser Ala Leu Tyr Leu Tyr Lys Asn Gly Glu Ile
                165                 170                 175

Asp Glu Tyr Glu Tyr Asn Phe Ser Ile Ser Ala Leu Asn Arg Arg Asp
            180                 185                 190

Asn Ile Ser Leu Phe Phe Phe Asp Ile Tyr Gly Tyr Tyr Ser Ser Asp
        195                 200                 205

Met Phe Val Ala Lys Asn Asn Glu Arg Val Met Leu Phe Ile Pro Gly
    210                 215                 220

Ala Lys Lys Pro Phe Leu Phe Glu Lys Asn Ile Ala Asp Leu Arg Ile
225                 230                 235                 240

Ser Leu Lys Asn Leu Ile Lys Glu Asn Asp Asn Lys Gln Leu Leu Ser
                245                 250                 255

Gln His Phe Ser Leu Tyr Ser Arg Gln Asp Gly Ile Thr Tyr Ala Gly
            260                 265                 270

Val Asn Ser Val Leu Asn Ala Ile Glu Asn Asp Gly Val Phe Asn Glu
        275                 280                 285

Ser Tyr Phe Leu Tyr Ser Asn Lys Arg Ile Asn Asn Lys Asp Val Phe
    290                 295                 300

Asp Ala Val Ala Phe Ser Val Lys Lys Arg Ser Phe Ser Asp Gly Asp
305                 310                 315                 320

Ile Val Ile Lys Ser Asn Ser Glu Ala Gln Arg Asp Tyr Ala Leu Thr
                325                 330                 335

Ile Leu Gln Thr Ile Leu Ser Met Thr Pro Ile Phe Asp Val Ala Ile
            340                 345                 350

Pro Glu Val Ser Val Thr Leu Gly Leu Gly Ile Ile Ala Ser Ser Met
        355                 360                 365

Gly Ile Ser Phe Asp Gln Leu Ile Asn Gly Asp Thr Tyr Glu Glu Arg
    370                 375                 380

Arg Ser Ala Ile Pro Gly Leu Ala Thr Asn Ala Ala Leu Leu Gly Leu
385                 390                 395                 400

Ser Phe Ala Ile Pro Phe Leu Ile Ser Lys Ala Gly Thr Asn Gln Lys
                405                 410                 415

Ile Leu Ser Arg Tyr Thr Lys His Glu Ile Arg Thr Leu Asn Glu Thr
            420                 425                 430

Asn Ile Asp Met Phe Leu Glu Glu Tyr Gly Ile Asn Lys Asn Ser Ile
        435                 440                 445
```

-continued

```
Ser Glu Thr Lys Val Leu Glu Val Glu Leu Lys Gly Ser Gly Gln His
    450                 455                 460

Val Asn Ile Val Lys Leu Ser Asp Glu Asp Asn Lys Ile Val Ala Val
465                 470                 475                 480

Lys Gly Asn Ser Leu Ser Gly Ile Tyr Tyr Glu Val Asp Ile Glu Thr
                    485                 490                 495

Gly Tyr Glu Ile Ser Ser Arg Arg Ile Tyr Arg Thr Glu Tyr Asn Asp
                500                 505                 510

Lys Ile Phe Trp Thr Arg Gly Gly Leu Lys Gly Gly Gln Ser Phe
            515                 520                 525

Asp Phe Glu Ser Leu Lys Leu Pro Ile Phe Phe Lys Asp Glu Pro Tyr
    530                 535                 540

Ser Ala Val Pro Gly Ser Ser Leu Ser Phe Ile Asn Asp Asp Ser Ser
545                 550                 555                 560

Leu Leu Tyr Pro Asn Ser Thr Pro Lys Leu Pro Gln Pro Thr Pro Glu
                    565                 570                 575

Met Glu Ile Val Asn Tyr Val Lys Arg Ala Gly Asn Phe Gly Glu Arg
                580                 585                 590

Leu Val Thr Leu Met Arg Gly Thr Thr Glu Glu Ala Trp Asn Ile
            595                 600                 605

Ala Arg Tyr His Thr Ala Gly Gly Ser Thr Glu Glu Leu His Glu Ile
    610                 615                 620

Leu Leu Gly Gln Gly Pro Gln Ser Ser Leu Gly Phe Thr Glu Tyr Thr
625                 630                 635                 640

Ser Asn Ile Asn Ser Ala Asp Ala Ala Ser Arg Arg His Phe Leu Val
                    645                 650                 655

Val Ile Lys Val Gln Val Lys Tyr Ile Asn Asn Asn Val Ser His
                660                 665                 670

Val Asn His Trp Ala Ile Pro Asp Glu Ala Pro Val Glu Val Leu Ala
            675                 680                 685

Val Val Asp Arg Arg Phe Asn Phe Pro Glu Pro Ser Thr Pro Pro Asn
    690                 695                 700

Ile Ser Ile Ile His Lys Leu Leu Ser Leu Arg Tyr Phe Lys Glu Asn
705                 710                 715                 720

Ile Glu Ser Thr Ser Arg Leu Asn Leu Gln Lys Leu Asn Arg Gly Asn
                    725                 730                 735

Ile Asp Ile Phe Lys Gly Arg Gly Ser Ile Ser Thr Arg Gln Arg
                740                 745                 750

Ala Ile Tyr Pro Tyr Phe Glu Ser Ala Asn Ala Asp Glu Gln Gln Pro
            755                 760                 765

Val Phe Phe Tyr Ile Lys Lys Asn Arg Phe Asp Asp Phe Gly Tyr Asp
    770                 775                 780

Gln Tyr Phe Tyr Asn Ser Thr Val Gly Leu Asn Gly Ile Pro Thr Leu
785                 790                 795                 800

Asn Thr Tyr Thr Gly Glu Ile Leu Ser Asp Ala Ser Ser Leu Gly Ser
                    805                 810                 815

Thr Tyr Trp Lys Lys Tyr Asn Leu Thr Asn Glu Thr Ser Ile Ile Arg
                820                 825                 830

Val Ser Asn Ser Ala Arg Gly Ala Asn Gly Ile Lys Ile Ala Leu Glu
            835                 840                 845

Glu Val Gln Glu Gly Lys Pro Val Ile Thr Ser Gly Asn Leu Ser
    850                 855                 860

Gly Cys Thr Thr Ile Val Ala Arg Lys Gly Gly Tyr Leu Tyr Lys Val
```

```
                865                 870                 875                 880
His Thr Gly Thr Thr Ile Pro Leu Ala Gly Phe Thr Ser Thr Thr Gly
                    885                 890                 895

Val Lys Lys Ala Val Glu Val Phe Glu Leu Leu Thr Asn Asn Pro Met
                900                 905                 910

Pro Arg Val Glu Gly Val Met Asn Asn Asp Phe Leu Val Asn Tyr Leu
                915                 920                 925

Ala Glu Ser Phe Asp Glu Ser Leu Ile Thr Tyr Ser Ser Glu Gln
            930                 935                 940

Lys Ile Gly Ser Lys Ile Thr Ile Ser Arg Asp Asn Val Ser Thr Phe
945                 950                 955                 960

Pro Tyr Phe Leu Asp Asn Ile Pro Glu Lys Gly Phe Gly Thr Ser Val
                965                 970                 975

Thr Ile Leu Val Arg Val Asp Gly Asn Val Ile Val Lys Ser Leu Ser
                980                 985                 990

Glu Ser Tyr Ser Leu Asn Val Glu Asn Ser Asn Ile Ser Val Leu His
            995                 1000                1005

Val Phe Ser Lys Asp Phe
    1010

<210> SEQ ID NO 3
<211> LENGTH: 1014
<212> TYPE: PRT
<213> ORGANISM: Yersinia pseudotuberculosis

<400> SEQUENCE: 3

Met Lys Asn Gln Trp Gln His Gln Tyr Phe Leu Ser Tyr Ser Glu Leu
1               5                   10                  15

Val Ala Asn Phe Pro Ser Pro Glu Lys Val Val Ser Asp Tyr Ile Lys
                20                  25                  30

His Lys Phe Ser Thr Thr Leu Pro Trp Phe Gly Trp Ala Asp Pro Asp
            35                  40                  45

Asn Leu Tyr Phe Ile Arg Phe Thr Gln Ser Arg Ser Asn Asn Lys Ser
    50                  55                  60

Tyr Thr Gly Trp Asp His Leu Gly Lys Tyr Ala Ile Glu Thr Leu Thr
65                  70                  75                  80

Leu Thr Gln Ala Ala Ile Val Asn Ile Gly Ser Arg Phe Asp Ile Phe
                85                  90                  95

Asp Glu Ala Asn Ser Thr Ala Gly Ile Tyr Lys Thr Asn Asn Ala Asp
                100                 105                 110

Ser Phe Asp Glu Thr Asn Glu Ala Lys Met Leu Pro Ser Glu Tyr Leu
            115                 120                 125

Tyr Phe Leu Arg Asp Cys Asp Phe Ser Asn Leu Tyr Asn Lys Ala Leu
    130                 135                 140

Ser Asp Tyr Trp Ala Glu Asn Tyr Glu Lys Phe Ser Thr Leu Leu Gln
145                 150                 155                 160

Asn Tyr Tyr Ile Ser Ser Ala Tyr Tyr Leu Tyr Lys Asp Ser Ala Ile
                165                 170                 175

Ser Lys Asp Glu Tyr Glu Phe Ser Ile Asp Ala Ile Phe Asn Lys Lys
            180                 185                 190

Ser Lys Ile Leu Arg Tyr Tyr Phe Asp Val Tyr Gly Tyr Tyr Ser Ser
    195                 200                 205

Asp Met Phe Val Ala Met Asn Asp Asn Lys Thr Met Leu Phe Ile Pro
210                 215                 220
```

-continued

```
Gly Ala Thr Asn Pro Phe Ile Phe Ala Asp Asn Ile Thr Asp Leu Arg
225                 230                 235                 240

Asp Lys Ile Lys Ala Leu Ile Ser Asp Lys Asn Thr Arg Glu Leu Phe
            245                 250                 255

Ser Lys His Phe Ser Leu Tyr Asp Arg Gln Asp Gly Asn Thr Tyr Leu
        260                 265                 270

Gly Val Asn Ser Met Leu Glu Gln Ile Val Ser Gly Val Val Asp Thr
    275                 280                 285

Asn Tyr Ile Met Tyr Ser Asn Lys Asn Ile Arg Glu Arg Asn Val Phe
290                 295                 300

Gly Ser Met Ala Phe Ser Thr Arg Glu Arg Ser Phe Asn Asp Gly Asp
305                 310                 315                 320

Val Ile Ile Lys Ser Asn Ala Glu Val Gln Arg Asp Tyr Ala Leu Asn
            325                 330                 335

Val Leu Gln Thr Ile Leu Ser Leu Ser Pro Ile Phe Asp Ile Val Leu
        340                 345                 350

Pro Glu Val Ser Ile Pro Ile Ser Leu Gly Ile Thr Ala Ser Ser Val
    355                 360                 365

Gly Ile Ser Phe Asp Glu Leu Ile Asn Gly Asp Thr Tyr Glu Glu Arg
370                 375                 380

Arg Ser Ala Ile Pro Gly Leu Ala Thr Asn Thr Val Leu Leu Gly Ile
385                 390                 395                 400

Ser Phe Ala Ile Pro Phe Leu Ile Ser Lys Ala Glu Asn Lys Leu
            405                 410                 415

Ile Ile Asn Asn Leu Val Gly Ser Asp Glu Asn Ile Leu Asn Lys Asn
        420                 425                 430

Asn Leu Gly Asp Phe Leu Glu Lys Tyr Asn Ile Ser Glu Ser Asp Ile
    435                 440                 445

Pro Glu Asn Gly Ser Leu Val Ile Asn Leu Lys Asn Thr Asn Val Pro
450                 455                 460

Val Arg Leu Val Lys Leu Asn Asp Glu Glu Gly Glu Ile Val Ala Ile
465                 470                 475                 480

Lys Gly Ser Thr Leu Ser Gly Ile Tyr Tyr Glu Val Asp Thr Glu Thr
            485                 490                 495

Gly Tyr Glu Ile Leu Ser Arg Arg Val Phe Arg Thr Glu Tyr Asn Glu
        500                 505                 510

Lys Ile Tyr Trp Thr Arg Gly Gly Leu Lys Gly Gly Gln Pro Phe
    515                 520                 525

Asn Phe Glu Gly Leu Asp Ile Pro Val Tyr Phe Ile Asp Lys Pro Tyr
530                 535                 540

Ser Glu Leu Ala Ser Ser Val Glu Leu Ser Phe Val Asn Asp Asp Ser
545                 550                 555                 560

Pro Leu Leu Phe Pro Glu Met Asp Ser Arg Leu Pro Lys Pro Thr Pro
            565                 570                 575

Glu Leu Asp Ile Lys Tyr Tyr Ser Ser Asn Leu Ser Ser Phe Lys Glu
        580                 585                 590

Asp Thr Val Ile Leu Met Arg Gly Thr Thr Glu Glu Ala Trp Asn
    595                 600                 605

Ile Ala Asn Tyr Lys Thr Ala Gly Gly Ser Asn Lys Asp Leu Glu Glu
610                 615                 620

Asn Phe Ile Glu Ala Gly Pro Gln Phe Asn Leu Ser Phe Ser Glu Tyr
625                 630                 635                 640

Thr Ser Ser Ile Asn Ser Ala Asp Thr Ala Ser Arg Lys His Phe Leu
```

```
                    645                 650                 655
Val Ile Ile Lys Val Gln Val Lys Tyr Ile Ser Asn Asp Asn Val Leu
                660                 665                 670

Tyr Ala Asn His Trp Ala Ile Pro Asp Glu Ala Pro Val Glu Val Leu
            675                 680                 685

Ala Val Val Asp Arg Arg Phe Ile Phe Pro Glu Pro Pro Val Lys Pro
        690                 695                 700

Lys Leu Ser Phe Ile Gln Lys Ile Ala Asn Arg Phe Leu Thr Glu Asn
705                 710                 715                 720

Val Ala Glu Ile Ser Ser Ile Asn Phe Arg Arg Leu Asn Ser Gly Asn
                725                 730                 735

Ile Asn Val Leu Lys Gly Arg Gly Val Phe Ser Ser Arg Arg Leu Arg
                740                 745                 750

Glu Ile Tyr Leu Arg Phe Asp Ala Ala Asn Ala Asp Glu Leu Arg Pro
            755                 760                 765

Gly Asp Val Tyr Val Lys Lys Thr Lys Phe Asp Ser Met Gly Tyr Asp
        770                 775                 780

Ser His Phe Tyr Asn Glu Gly Ile Gly Ile Asn Gly Ala Pro Thr Leu
785                 790                 795                 800

Asn Thr Tyr Thr Gly Glu Tyr Val Ala Asp Ser Ser Gln Gly Ala
                805                 810                 815

Thr Tyr Trp Leu Lys Tyr Asn Leu Thr Asn Glu Thr Ser Ile Ile Lys
                820                 825                 830

Val Ser Asn Ser Ala Arg Gly Ala Asn Gly Ile Lys Ile Ala Leu Glu
            835                 840                 845

Glu Ile Glu Glu Asn Lys Pro Val Val Ile Thr Ser Gly Thr Leu Thr
        850                 855                 860

Gly Cys Thr Val Val Phe Ala Arg Lys Gly Leu Tyr Phe Tyr Ala Val
865                 870                 875                 880

His Thr Gly Asn Ser Glu Ser Leu Ile Gly Phe Thr Ser Thr Ser Gly
                885                 890                 895

Val Ala Lys Ala Ile Glu Val Leu Ser Ser Leu Ser Glu Leu Glu Val
            900                 905                 910

Pro Ala Leu Pro Asp Val Ile Asn Asn Asn Thr Leu Val Glu Tyr Leu
        915                 920                 925

Ser Asp Asn Phe Asp Ser Ala Leu Ile Ser Tyr Ser Ser Ser Ser Leu
        930                 935                 940

Lys Pro Asn Ser Met Ile Asn Ile Ser Arg Glu Asn Val Ser Thr Phe
945                 950                 955                 960

Ser Tyr Tyr Thr Asp Asp Ile Gln Leu Pro Ser Phe Gly Thr Ser Val
                965                 970                 975

Thr Ile Leu Val Arg Thr Asn Asp Asn Thr Val Val Arg Ser Leu Ser
            980                 985                 990

Glu Ser Tyr Thr Met Asn Ser Asn Ser Ser Lys Met Val Leu Phe Asn
            995                 1000                1005

Val Leu Gln Lys Asp Phe
    1010

<210> SEQ ID NO 4
<211> LENGTH: 1451
<212> TYPE: PRT
<213> ORGANISM: Bordetella pertussis

<400> SEQUENCE: 4
```

-continued

```
Met Ala Leu Val Gly Tyr Asp Gly Val Glu Leu Leu Ala Leu
 1               5                  10                  15
Pro Ser Glu Glu Ser Gly Asp Leu Ala Gly Gly Arg Ala Lys Arg Glu
                 20                  25                  30
Lys Ala Glu Phe Ala Leu Phe Ser Glu Ala Pro Asn Gly Asp Glu Pro
             35                  40                  45
Ile Gly Gln Asp Ala Arg Thr Trp Phe Tyr Phe Pro Lys Tyr Arg Pro
         50                  55                  60
Val Ala Val Ser Asn Leu Lys Lys Met Gln Val Ala Ile Arg Ala Arg
 65                  70                  75                  80
Leu Glu Pro Glu Ser Leu Ile Leu Gln Trp Leu Ile Ala Leu Asp Val
                 85                  90                  95
Tyr Leu Gly Val Leu Ile Ala Ala Leu Ser Arg Thr Val Ile Ser Asp
             100                 105                 110
Leu Val Phe Glu Tyr Val Lys Ala Arg Tyr Glu Ile Tyr Tyr Leu Leu
         115                 120                 125
Asn Arg Val Pro His Pro Leu Ala Thr Ala Tyr Leu Lys Arg Arg Arg
     130                 135                 140
Gln Arg Pro Val Asp Arg Ser Gly Arg Leu Gly Ser Val Phe Glu His
145                 150                 155                 160
Pro Leu Trp Phe Ala Tyr Asp Glu Leu Ala Gly Thr Val Asp Leu Asp
                 165                 170                 175
Ala Asp Ile Tyr Glu Gln Ala Leu Ala Glu Ser Ile Glu Arg Arg Met
             180                 185                 190
Asp Gly Glu Pro Asp Asp Gly Ser Leu Asp Thr Ala Glu His Asp Val
         195                 200                 205
Trp Arg Leu Cys Arg Asp Gly Ile Asn Arg Gly Glu Gln Ala Ile Phe
     210                 215                 220
Gln Ala Ser Gly Pro Tyr Gly Val Val Ala Asp Ala Gly Tyr Met Arg
225                 230                 235                 240
Thr Val Ala Asp Leu Ala Tyr Ala Asp Ala Leu Ala Asp Cys Leu His
                 245                 250                 255
Ala Gln Leu Arg Ile Arg Ala Gln Gly Ser Val Asp Ser Pro Gly Asp
             260                 265                 270
Glu Met Pro Arg Lys Leu Asp Ala Trp Glu Ile Ala Lys Phe His Leu
         275                 280                 285
Ala Ala Thr Gln Gln Ala Arg Val Asp Leu Leu Glu Ala Ala Phe Ala
     290                 295                 300
Leu Asp Tyr Ala Ala Leu Arg Asp Val Arg Val Tyr Gly Asp Tyr Arg
305                 310                 315                 320
Asn Ala Leu Ala Leu Arg Phe Ile Lys Arg Glu Ala Leu Arg Leu Leu
                 325                 330                 335
Gly Ala Arg Arg Gly Asn Ala Ser Thr Met Pro Ala Val Ala Ala Gly
             340                 345                 350
Glu Tyr Asp Glu Ile Val Ala Ser Gly Ala Ala Asn Asp Ala Ala Tyr
         355                 360                 365
Val Ser Met Ala Ala Ala Leu Ile Ala Gly Val Leu Cys Asp Leu Glu
     370                 375                 380
Ser Ala Gln Arg Thr Leu Pro Val Val Leu Ala Arg Phe Arg Pro Leu
385                 390                 395                 400
Gly Val Leu Ala Arg Phe Arg Arg Leu Glu Gln Glu Thr Ala Gly Met
                 405                 410                 415
Leu Leu Gly Asp Gln Glu Pro Glu Pro Arg Gly Phe Ile Ser Phe Thr
```

-continued

```
            420                 425                 430
Asp Phe Arg Asp Ser Asp Ala Phe Ala Ser Tyr Ala Glu Tyr Ala Ala
        435                 440                 445

Gln Phe Asn Asp Tyr Ile Asp Gln Tyr Ser Ile Leu Glu Ala Gln Arg
    450                 455                 460

Leu Ala Arg Ile Leu Ala Leu Gly Ser Arg Met Thr Val Asp Gln Trp
465                 470                 475                 480

Cys Leu Pro Leu Gln Lys Val Arg His Tyr Lys Val Leu Thr Ser Gln
                485                 490                 495

Pro Gly Leu Ile Ala Arg Gly Ile Glu Asn His Asn Arg Gly Ile Glu
            500                 505                 510

Tyr Cys Leu Gly Arg Pro Pro Leu Thr Asp Leu Pro Gly Leu Phe Thr
        515                 520                 525

Met Phe Gln Leu His Asp Ser Ser Trp Leu Leu Val Ser Asn Ile Asn
    530                 535                 540

Gly Glu Leu Trp Ser Asp Val Leu Ala Asn Ala Glu Val Met Gln Asn
545                 550                 555                 560

Pro Thr Leu Ala Ala Leu Ala Glu Pro Gln Gly Arg Phe Arg Thr Gly
                565                 570                 575

Arg Arg Thr Gly Gly Trp Phe Leu Gly Gly Pro Ala Thr Glu Gly Pro
            580                 585                 590

Ser Leu Arg Asp Asn Tyr Leu Leu Lys Leu Arg Gln Ser Asn Pro Gly
        595                 600                 605

Leu Asp Val Lys Lys Cys Trp Tyr Phe Gly Tyr Arg Gln Glu Tyr Arg
610                 615                 620

Leu Pro Ala Gly Ala Leu Gly Val Pro Leu Phe Ala Val Ser Val Ala
625                 630                 635                 640

Leu Arg His Ser Leu Asp Asp Leu Ala Ala His Ala Lys Ser Ala Leu
                645                 650                 655

Tyr Lys Pro Ser Glu Trp Gln Lys Phe Ala Phe Trp Ile Val Pro Phe
            660                 665                 670

Tyr Arg Glu Ile Phe Phe Ser Thr Gln Asp Arg Ser Tyr Arg Val Asp
        675                 680                 685

Val Gly Ser Ile Val Phe Asp Ser Ile Ser Leu Leu Ala Ser Val Phe
690                 695                 700

Ser Ile Gly Gly Lys Leu Gly Ser Phe Thr Arg Thr Gln Tyr Gly Asn
705                 710                 715                 720

Leu Arg Asn Phe Val Val Arg Gln Arg Ile Ala Gly Leu Ser Gly Gln
                725                 730                 735

Arg Leu Trp Arg Ser Val Leu Lys Glu Leu Pro Ala Leu Ile Gly Ala
            740                 745                 750

Ser Gly Leu Arg Leu Ser Arg Ser Leu Leu Val Asp Leu Tyr Glu Ile
        755                 760                 765

Phe Glu Pro Val Pro Ile Arg Arg Leu Val Ala Gly Phe Val Ser Ala
    770                 775                 780

Thr Thr Val Gly Gly Arg Asn Gln Ala Phe Leu Arg Gln Ala Phe Ser
785                 790                 795                 800

Ala Ala Ser Ser Ser Ala Gly Arg Thr Gly Gly Gln Leu Ala Ser Glu
                805                 810                 815

Trp Arg Met Ala Gly Val Asp Ala Thr Gly Leu Val Glu Ser Thr Ser
            820                 825                 830

Gly Gly Arg Phe Glu Gly Ile Tyr Thr Arg Gly Leu Gly Pro Leu Ser
        835                 840                 845
```

-continued

Glu Cys Thr Glu His Phe Ile Val Glu Ser Gly Asn Ala Tyr Arg Val
850                 855                 860

Ile Trp Asp Ala Tyr Thr His Gly Trp Arg Val Val Asn Gly Arg Leu
865                 870                 875                 880

Pro Pro Arg Leu Thr Tyr Thr Val Pro Val Arg Leu Asn Gly Gln Gly
                885                 890                 895

His Trp Glu Thr His Leu Asp Val Pro Gly Arg Gly Gly Ala Pro Glu
            900                 905                 910

Ile Phe Gly Arg Ile Arg Thr Arg Asn Leu Val Ala Leu Ala Ala Glu
                915                 920                 925

Gln Ala Ala Pro Met Arg Arg Leu Leu Asn Gln Ala Arg Arg Val Ala
930                 935                 940

Leu Arg His Ile Asp Thr Cys Arg Ser Arg Leu Ala Leu Pro Arg Ala
945                 950                 955                 960

Glu Ser Asp Met Asp Ala Ala Ile Arg Ile Phe Phe Gly Glu Pro Asp
                965                 970                 975

Ala Gly Leu Arg Gln Arg Ile Gly Arg Arg Leu Gln Glu Val Arg Ala
            980                 985                 990

Tyr Ile Gly Asp Leu Ser Pro Val Asn Asp Val Leu Tyr Arg Ala Gly
                995                 1000                1005

Tyr Asp Leu Asp Asp Val Ala Thr Leu Phe Asn Ala Val Asp Arg Asn
    1010                1015                1020

Thr Ser Leu Gly Arg Gln Ala Arg Met Glu Leu Tyr Leu Asp Ala Ile
1025                1030                1035                1040

Val Asp Leu His Ala Arg Leu Gly Tyr Glu Asn Ala Arg Phe Val Asp
                1045                1050                1055

Leu Met Ala Phe His Leu Leu Ser Leu Gly His Ala Ala Thr Ala Ser
            1060                1065                1070

Glu Val Val Glu Ala Val Ser Pro Arg Leu Leu Gly Asn Val Phe Asp
            1075                1080                1085

Ile Ser Asn Val Ala Gln Leu Glu Arg Gly Ile Gly Asn Pro Ala Ser
    1090                1095                1100

Thr Gly Leu Phe Val Met Leu Gly Ala Tyr Ser Glu Ser Ser Pro Ala
1105                1110                1115                1120

Ile Phe Gln Ser Phe Val Asn Asp Ile Phe Pro Ala Trp Arg Gln Ala
                1125                1130                1135

Ser Gly Gly Gly Pro Leu Val Trp Asn Phe Gly Pro Ala Ala Ile Ser
            1140                1145                1150

Pro Thr Arg Leu Asp Tyr Ala Asn Thr Asp Ile Gly Leu Leu Asn His
            1155                1160                1165

Gly Asp Ile Ser Pro Leu Arg Ala Arg Pro Pro Leu Gly Gly Arg Arg
    1170                1175                1180

Asp Ile Asp Leu Pro Pro Gly Leu Asp Ile Ser Phe Val Arg Tyr Asp
1185                1190                1195                1200

Arg Pro Val Arg Met Ser Ala Pro Arg Ala Leu Asp Ala Ser Val Phe
                1205                1210                1215

Arg Pro Val Asp Gly Pro Val His Gly Tyr Ile Gln Ser Trp Thr Gly
            1220                1225                1230

Ala Glu Ile Glu Tyr Ala Tyr Gly Ala Pro Ala Ala Ala Arg Glu Val
    1235                1240                1245

Met Leu Thr Asp Asn Val Arg Ile Ile Ser Ile Glu Asn Gly Asp Glu
1250                1255                1260

```
Gly Ala Ile Gly Val Arg Val Arg Leu Asp Thr Val Pro Val Ala Thr
1265                1270                1275                1280

Pro Leu Ile Leu Thr Gly Gly Ser Leu Ser Gly Cys Thr Thr Met Val
            1285                1290                1295

Gly Val Lys Glu Gly Tyr Leu Ala Phe Tyr His Thr Gly Lys Ser Thr
        1300                1305                1310

Glu Leu Gly Asp Trp Ala Thr Ala Arg Glu Gly Val Gln Ala Leu Tyr
    1315                1320                1325

Gln Ala His Leu Ala Met Gly Tyr Ala Pro Ile Ser Ile Pro Ala Pro
1330                1335                1340

Met Arg Asn Asp Asp Leu Val Ser Ile Ala Ala Thr Tyr Asp Arg Ala
1345                1350                1355                1360

Val Ile Ala Tyr Leu Gly Lys Asp Val Pro Gly Gly Gly Ser Thr Arg
            1365                1370                1375

Ile Thr Arg His Asp Glu Gly Ala Gly Ser Val Val Ser Phe Asp Tyr
        1380                1385                1390

Asn Ala Ala Val Gln Ala Ser Ala Val Pro Arg Leu Gly Gln Val Tyr
    1395                1400                1405

Val Leu Ile Ser Asn Asp Gly Gln Gly Ala Arg Ala Val Leu Leu Ala
1410                1415                1420

Glu Asp Leu Ala Trp Ala Gly Ser Gly Ser Ala Leu Asp Val Leu Asn
1425                1430                1435                1440

Glu Arg Leu Val Thr Leu Phe Pro Ala Pro Val
            1445                1450

<210> SEQ ID NO 5
<211> LENGTH: 240
<212> TYPE: PRT
<213> ORGANISM: Salmonella typhimurium

<400> SEQUENCE: 5

Met Thr Lys Ile Thr Leu Ser Pro Gln Asn Phe Arg Ile Gln Lys Gln
1               5                   10                  15

Glu Thr Thr Leu Leu Lys Glu Lys Ser Thr Glu Lys Asn Ser Leu Ala
            20                  25                  30

Lys Ser Ile Leu Ala Val Lys Asn His Phe Ile Glu Leu Arg Ser Lys
        35                  40                  45

Leu Ser Glu Arg Phe Ile Ser His Lys Asn Thr Glu Ser Ser Ala Thr
    50                  55                  60

His Phe His Arg Gly Ser Ala Ser Glu Gly Arg Ala Val Leu Thr Asn
65                  70                  75                  80

Lys Val Val Lys Asp Phe Met Leu Gln Thr Leu Asn Asp Ile Asp Ile
                85                  90                  95

Arg Gly Ser Ala Ser Lys Asp Pro Ala Tyr Ala Ser Gln Thr Arg Glu
            100                 105                 110

Ala Ile Leu Ser Ala Val Tyr Ser Lys Asn Lys Asp Gln Cys Cys Asn
        115                 120                 125

Leu Leu Ile Ser Lys Gly Ile Asn Ile Ala Pro Phe Leu Gln Glu Ile
    130                 135                 140

Gly Glu Ala Ala Lys Asn Ala Gly Leu Pro Gly Thr Thr Lys Asn Asp
145                 150                 155                 160

Val Phe Thr Pro Ser Gly Ala Gly Ala Asn Pro Phe Ile Thr Pro Leu
                165                 170                 175

Ile Ser Ser Ala Asn Ser Lys Tyr Pro Arg Met Phe Ile Asn Gln His
            180                 185                 190
```

```
Gln Gln Ala Ser Phe Lys Ile Tyr Ala Glu Lys Ile Ile Met Thr Glu
            195                 200                 205

Val Ala Pro Leu Phe Asn Glu Cys Ala Met Pro Thr Pro Gln Gln Phe
        210                 215                 220

Gln Leu Ile Leu Glu Asn Ile Ala Asn Lys Tyr Ile Gln Tyr Thr Pro
225                 230                 235                 240

<210> SEQ ID NO 6
<211> LENGTH: 240
<212> TYPE: PRT
<213> ORGANISM: Salmonella typhimurium

<400> SEQUENCE: 6

Met Thr Asn Ile Thr Leu Ser Thr Gln His Tyr Arg Ile His Arg Ser
  1               5                  10                  15

Asp Val Glu Pro Val Lys Glu Lys Thr Thr Glu Lys Asp Ile Phe Ala
             20                  25                  30

Lys Ser Ile Thr Ala Val Arg Asn Ser Phe Ile Ser Leu Ser Thr Ser
         35                  40                  45

Leu Ser Asp Arg Phe Ser Leu His Gln Gln Thr Asp Ile Pro Thr Thr
 50                  55                  60

His Phe His Arg Gly Asn Ala Ser Glu Gly Arg Ala Val Leu Thr Ser
 65                  70                  75                  80

Lys Thr Val Lys Asp Phe Met Leu Gln Lys Leu Asn Ser Leu Asp Ile
                 85                  90                  95

Lys Gly Asn Ala Ser Lys Asp Pro Ala Tyr Ala Arg Gln Thr Cys Glu
            100                 105                 110

Ala Ile Leu Ser Ala Val Tyr Ser Asn Asn Lys Asp Gln Cys Cys Lys
        115                 120                 125

Leu Leu Ile Ser Lys Gly Val Ser Ile Thr Pro Phe Leu Lys Glu Ile
130                 135                 140

Gly Glu Ala Ala Gln Asn Ala Gly Leu Pro Gly Glu Ile Lys Asn Gly
145                 150                 155                 160

Val Phe Thr Pro Gly Gly Ala Gly Ala Asn Pro Phe Val Val Pro Leu
                165                 170                 175

Ile Ala Ser Ala Ser Ile Lys Tyr Pro His Met Phe Ile Asn His Asn
            180                 185                 190

Gln Gln Val Ser Phe Lys Ala Tyr Ala Glu Lys Ile Val Met Lys Glu
        195                 200                 205

Val Thr Pro Leu Phe Asn Lys Gly Thr Met Pro Thr Pro Gln Gln Phe
    210                 215                 220

Gln Leu Thr Ile Glu Asn Ile Ala Asn Lys Tyr Leu Gln Asn Ala Ser
225                 230                 235                 240

<210> SEQ ID NO 7
<211> LENGTH: 166
<212> TYPE: PRT
<213> ORGANISM: Shigella flexneri

<400> SEQUENCE: 7

Met Glu Ile Gln Asn Thr Lys Ser Ala Pro Ile Leu Tyr Thr Asp Ile
  1               5                  10                  15

Ser Thr Lys Gln Thr Gln Ser Ser Glu Thr Gln Lys Ser Gln Asn
             20                  25                  30

Tyr Gln Gln Leu Ala Ala His Ile Pro Leu Asn Val Gly Lys Asn Pro
         35                  40                  45
```

```
Val Leu Thr Thr Thr Leu Asn Asp Asp Gln Leu Leu Lys Leu Ser Glu
         50                  55                  60

Gln Val Gln His Asp Ser Glu Ile Ile Ala Arg Leu Thr Asp Lys Lys
 65                  70                  75                  80

Met Lys Asp Leu Ser Glu Met Ser His Thr Ile Thr Pro Glu Asn Thr
                 85                  90                  95

Leu Asp Ile Ser Ser Leu Ser Ser Asn Ala Val Ser Leu Ile Ile Ser
                100                 105                 110

Val Ala Val Leu Leu Ser Ala Leu Arg Thr Ala Glu Thr Arg Leu Gly
                115                 120                 125

Ser Gln Leu Ser Leu Ile Ala Phe Asp Ala Thr Lys Ser Ala Ala Glu
        130                 135                 140

Asn Ile Val Arg Gln Gly Leu Ala Ala Leu Ser Ser Ile Thr Gly
145                 150                 155                 160

Ala Val Thr Gln Val Gly
                165
```

<210> SEQ ID NO 8
<211> LENGTH: 1186
<212> TYPE: PRT
<213> ORGANISM: Helicobacter pylori

<400> SEQUENCE: 8

```
Met Thr Asn Glu Thr Ile Asp Gln Thr Arg Thr Pro Asp Gln Thr Gln
  1               5                  10                  15

Ser Gln Thr Ala Phe Asp Pro Gln Gln Phe Ile Asn Asn Leu Gln Val
                 20                  25                  30

Ala Phe Ile Lys Val Asp Asn Val Val Ala Ser Phe Asp Pro Asp Gln
             35                  40                  45

Lys Pro Ile Val Asp Lys Asn Asp Arg Asp Asn Arg Gln Ala Phe Asp
         50                  55                  60

Gly Ile Ser Gln Leu Arg Glu Glu Tyr Ser Asn Lys Ala Ile Lys Asn
 65                  70                  75                  80

Pro Thr Lys Lys Asn Gln Tyr Phe Ser Asp Phe Ile Asp Lys Ser Asn
                 85                  90                  95

Asp Leu Ile Asn Lys Asp Asn Leu Ile Asp Val Glu Ser Ser Thr Lys
                100                 105                 110

Ser Phe Gln Lys Phe Gly Asp Gln Arg Tyr Gln Ile Phe Thr Ser Trp
        115                 120                 125

Val Ser His Gln Lys Asp Pro Ser Lys Ile Asn Thr Arg Ser Ile Arg
    130                 135                 140

Asn Phe Met Glu Asn Ile Ile Gln Pro Ile Pro Asp Asp Lys Glu
145                 150                 155                 160

Lys Ala Glu Phe Leu Lys Ser Ala Lys Gln Ser Phe Ala Gly Ile Ile
                165                 170                 175

Ile Gly Asn Gln Ile Arg Thr Asp Gln Lys Phe Met Gly Val Phe Asp
            180                 185                 190

Glu Ser Leu Lys Glu Arg Gln Glu Ala Glu Lys Asn Gly Gly Pro Thr
        195                 200                 205

Gly Gly Asp Trp Leu Asp Ile Phe Leu Ser Phe Ile Phe Asn Lys Lys
    210                 215                 220

Gln Ser Ser Asp Val Lys Glu Ala Ile Asn Gln Glu Pro Val Pro His
225                 230                 235                 240

Val Gln Pro Asp Ile Ala Thr Thr Thr Thr Asp Ile Gln Gly Leu Pro
```

-continued

```
                245                 250                 255
Pro Glu Ala Arg Asp Leu Leu Asp Glu Arg Gly Asn Phe Ser Lys Phe
            260                 265                 270

Thr Leu Gly Asp Met Glu Met Leu Asp Val Glu Gly Val Ala Asp Ile
        275                 280                 285

Asp Pro Asn Tyr Lys Phe Asn Gln Leu Leu Ile His Asn Asn Ala Leu
    290                 295                 300

Ser Ser Val Leu Met Gly Ser His Asn Gly Ile Glu Pro Glu Lys Val
305                 310                 315                 320

Ser Leu Leu Tyr Ala Gly Asn Gly Gly Phe Gly Asp Lys His Asp Trp
            325                 330                 335

Asn Ala Thr Val Gly Tyr Lys Asp Gln Gln Gly Asn Asn Val Ala Thr
        340                 345                 350

Leu Ile Asn Val His Met Lys Asn Gly Ser Gly Leu Val Ile Ala Gly
    355                 360                 365

Gly Glu Lys Gly Ile Asn Asn Pro Ser Phe Tyr Leu Tyr Lys Glu Asp
    370                 375                 380

Gln Leu Thr Gly Ser Gln Arg Ala Leu Ser Gln Glu Glu Ile Arg Asn
385                 390                 395                 400

Lys Val Asp Phe Met Glu Phe Leu Ala Gln Asn Asn Thr Lys Leu Asp
            405                 410                 415

Asn Leu Ser Glu Lys Glu Lys Glu Lys Phe Gln Asn Glu Ile Glu Asp
        420                 425                 430

Phe Gln Lys Asp Ser Lys Ala Tyr Leu Asp Ala Leu Gly Asn Asp Arg
    435                 440                 445

Ile Ala Phe Val Ser Lys Lys Asp Thr Lys His Ser Ala Leu Ile Thr
450                 455                 460

Glu Phe Asn Asn Gly Asp Leu Ser Tyr Thr Leu Lys Asp Tyr Gly Lys
465                 470                 475                 480

Lys Ala Asp Lys Ala Leu Asp Arg Glu Lys Asn Val Thr Leu Gln Gly
            485                 490                 495

Ser Leu Lys His Asp Gly Val Met Phe Val Asp Tyr Ser Asn Phe Lys
        500                 505                 510

Tyr Thr Asn Ala Ser Lys Asn Pro Asn Lys Gly Val Gly Ala Thr Asn
    515                 520                 525

Gly Val Ser His Leu Glu Ala Gly Phe Asn Lys Val Ala Val Phe Asn
530                 535                 540

Leu Pro Asp Leu Asn Asn Leu Ala Ile Thr Ser Phe Val Arg Arg Asn
545                 550                 555                 560

Leu Glu Asn Lys Leu Thr Ala Lys Gly Leu Ser Leu Gln Glu Ala Asn
            565                 570                 575

Lys Leu Ile Lys Asp Phe Leu Ser Ser Asn Lys Glu Leu Ala Gly Lys
        580                 585                 590

Ala Leu Asn Phe Asn Lys Ala Val Ala Glu Ala Lys Ser Thr Gly Asn
    595                 600                 605

Tyr Asp Glu Val Lys Lys Ala Gln Lys Asp Leu Glu Lys Ser Leu Arg
    610                 615                 620

Lys Arg Glu His Leu Glu Lys Glu Val Glu Lys Leu Glu Ser Lys
625                 630                 635                 640

Ser Gly Asn Lys Asn Lys Met Glu Ala Lys Ala Gln Ala Asn Ser Gln
            645                 650                 655

Lys Asp Glu Ile Phe Ala Leu Ile Asn Lys Glu Ala Asn Arg Asp Ala
        660                 665                 670
```

```
Arg Ala Ile Ala Tyr Thr Gln Asn Leu Lys Gly Ile Lys Arg Glu Leu
            675                 680                 685

Ser Asp Lys Leu Glu Lys Ile Ser Lys Asp Leu Lys Asp Phe Ser Lys
        690                 695                 700

Ser Phe Asp Glu Phe Lys Asn Gly Lys Asn Lys Asp Phe Ser Lys Ala
705                 710                 715                 720

Glu Glu Thr Leu Lys Ala Leu Lys Gly Ser Val Lys Asp Leu Gly Ile
                725                 730                 735

Asn Pro Glu Trp Ile Ser Lys Val Glu Asn Leu Asn Ala Ala Leu Asn
            740                 745                 750

Glu Phe Lys Asn Gly Lys Asn Lys Asp Phe Ser Lys Val Thr Gln Ala
        755                 760                 765

Lys Ser Asp Leu Glu Asn Ser Val Lys Asp Val Ile Ile Asn Gln Lys
    770                 775                 780

Val Thr Asp Lys Val Asp Asn Leu Asn Gln Ala Val Ser Val Ala Lys
785                 790                 795                 800

Ala Met Gly Asp Phe Ser Arg Val Gln Val Leu Ala Asp Leu Lys
                805                 810                 815

Asn Phe Ser Lys Glu Gln Leu Ala Gln Ala Gln Lys Asn Glu Asp
            820                 825                 830

Phe Asn Thr Gly Lys Asn Ser Glu Leu Tyr Gln Ser Val Lys Asn Ser
        835                 840                 845

Val Asn Lys Thr Leu Val Gly Asn Gly Leu Ser Gly Ile Glu Ala Thr
    850                 855                 860

Ala Leu Ala Lys Asn Phe Ser Asp Ile Lys Lys Glu Leu Asn Glu Lys
865                 870                 875                 880

Phe Lys Asn Phe Asn Asn Asn Asn Gly Leu Lys Asn Ser Thr Glu
                885                 890                 895

Pro Ile Tyr Ala Lys Val Asn Lys Lys Thr Gly Gln Val Ala Ser
            900                 905                 910

Pro Glu Glu Pro Ile Tyr Thr Gln Val Ala Lys Lys Val Asn Ala Lys
        915                 920                 925

Ile Asp Arg Leu Asn Gln Ile Ala Ser Gly Leu Gly Gly Val Gly Gln
    930                 935                 940

Ala Ala Gly Phe Pro Leu Lys Arg His Asp Lys Val Asp Asp Leu Ser
945                 950                 955                 960

Lys Val Gly Leu Ser Ala Ser Pro Glu Pro Ile Tyr Ala Thr Ile Asp
                965                 970                 975

Asp Leu Gly Gly Pro Phe Pro Leu Lys Arg His Asp Lys Val Asp Asp
            980                 985                 990

Leu Ser Lys Val Gly Arg Ser Arg Asn Gln Glu Leu Ala Gln Lys Ile
        995                 1000                1005

Asp Asn Leu Asn Gln Ala Val Ser Glu Ala Lys Ala Gly Phe Phe Gly
    1010                1015                1020

Asn Leu Glu Gln Thr Ile Asp Lys Leu Lys Asp Ser Thr Lys Lys Asn
1025                1030                1035                1040

Val Met Asn Leu Tyr Val Glu Ser Ala Lys Lys Val Pro Ala Ser Leu
                1045                1050                1055

Ser Ala Lys Leu Asp Asn Tyr Ala Ile Asn Ser His Thr Arg Ile Asn
            1060                1065                1070

Ser Asn Ile Gln Asn Gly Ala Ile Asn Glu Lys Ala Thr Gly Met Leu
        1075                1080                1085
```

```
Thr Gln Lys Asn Pro Glu Trp Leu Lys Leu Val Asn Asp Lys Ile Val
    1090                1095                1100

Ala His Asn Val Gly Ser Val Ser Leu Ser Glu Tyr Asp Lys Ile Gly
1105                1110                1115                1120

Phe Asn Gln Lys Asn Met Lys Asp Tyr Ser Asp Ser Phe Lys Phe Ser
                1125                1130                1135

Thr Lys Leu Asn Asn Ala Val Lys Asp Ile Lys Ser Gly Phe Thr His
        1140                1145                1150

Phe Leu Ala Asn Ala Phe Ser Thr Gly Tyr Tyr Cys Leu Ala Arg Glu
    1155                1160                1165

Asn Ala Glu His Gly Ile Lys Asn Val Asn Thr Lys Gly Gly Phe Gln
    1170                1175                1180

Lys Ser
1185

<210> SEQ ID NO 9
<211> LENGTH: 201
<212> TYPE: PRT
<213> ORGANISM: Homo sapiens

<400> SEQUENCE: 9

Ser Ser Gly Pro Ser Ser Leu Asp Asn Gly Asn Ser Leu Asp Val
1               5                   10                  15

Leu Lys Asn His Val Leu Asn Glu Leu Ile Gln Thr Glu Arg Val Tyr
            20                  25                  30

Val Arg Glu Leu Tyr Thr Val Leu Leu Gly Tyr Arg Ala Glu Met Asp
        35                  40                  45

Asn Pro Glu Met Phe Asp Leu Met Pro Leu Leu Arg Asn Lys Lys
    50                  55                  60

Asp Ile Leu Phe Gly Asn Met Ala Glu Ile Tyr Glu Phe His Asn Asp
65                  70                  75                  80

Ile Phe Leu Ser Ser Leu Glu Asn Cys Ala His Ala Pro Glu Arg Val
                85                  90                  95

Gly Pro Cys Phe Leu Glu Arg Lys Asp Asp Phe Gln Met Tyr Ala Lys
            100                 105                 110

Tyr Cys Gln Asn Lys Pro Arg Ser Glu Thr Ile Trp Arg Lys Tyr Ser
        115                 120                 125

Glu Cys Ala Phe Phe Gln Glu Cys Gln Arg Lys Leu Lys His Arg Leu
    130                 135                 140

Arg Leu Asp Ser Tyr Leu Leu Lys Pro Val Gln Arg Ile Thr Lys Tyr
145                 150                 155                 160

Gln Leu Leu Leu Lys Glu Leu Leu Lys Tyr Ser Lys Asp Cys Glu Gly
                165                 170                 175

Ser Ala Leu Leu Lys Lys Ala Leu Asp Ala Met Leu Asp Leu Leu Lys
            180                 185                 190

Ser Val Asn Asp Ser Met His Gln Ile
        195                 200
```